United States Patent
Haefner

(10) Patent No.: US 7,996,072 B2
(45) Date of Patent: Aug. 9, 2011

(54) POSITIONALLY ADAPTABLE IMPLANTABLE CARDIAC DEVICE

(75) Inventor: Paul Allan Haefner, Circle Pines, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 939 days.

(21) Appl. No.: 11/019,497

(22) Filed: Dec. 21, 2004

(65) Prior Publication Data

US 2006/0167502 A1    Jul. 27, 2006

(51) Int. Cl.
*A61N 1/39* (2006.01)

(52) U.S. Cl. .................... 600/512; 607/4; 607/36

(58) Field of Classification Search ............... 600/512, 600/509; 607/4, 36
See application file for complete search history.

(56) References Cited

U.S. PATENT DOCUMENTS

| | | | |
|---|---|---|---|
| 4,091,818 A | 5/1978 | Brownlee et al. |
| 4,414,982 A | 11/1983 | Durkan |
| 4,562,841 A | 1/1986 | Brockway et al. |
| 4,813,427 A | 3/1989 | Schlaefke et al. |
| 4,830,008 A | 5/1989 | Meer |
| 4,836,219 A | 6/1989 | Hobson et al. |
| 4,856,524 A | 8/1989 | Baker, Jr. |
| 4,953,551 A | 9/1990 | Mehra et al. |
| 5,024,222 A | 6/1991 | Thacker |
| 5,036,849 A | 8/1991 | Hauck et al. |
| 5,133,353 A | 7/1992 | Hauser |
| 5,170,784 A | 12/1992 | Ramon et al. |
| 5,179,945 A | 1/1993 | Van Hofwegen et al. |
| 5,203,348 A | 4/1993 | Dahl et al. |
| 5,209,229 A | 5/1993 | Gilli |
| 5,211,173 A | 5/1993 | Kallok et al. |
| 5,215,082 A | 6/1993 | Kallok et al. |
| 5,230,337 A | 7/1993 | Dahl et al. |
| 5,245,995 A | 9/1993 | Sullivan et al. |
| 5,261,400 A | 11/1993 | Bardy |
| 5,280,791 A | 1/1994 | Lavie |

(Continued)

FOREIGN PATENT DOCUMENTS

EP     0750920     1/1997

(Continued)

OTHER PUBLICATIONS

Aircraft Noise and Sleep Disturbance final report, http/www.caa.co.uk/docs/33/ERCD%208008.pdf.

(Continued)

*Primary Examiner* — Carl H Layno
*Assistant Examiner* — Jennifer Stewart
(74) *Attorney, Agent, or Firm* — Hollingsworth & Funk, LLC

(57) ABSTRACT

Cardiac sensing and/or stimulation devices and methods that adapt to implant location and positioning, and may employ automated vector selection from multiple electrodes. Devices include a housing having a first face opposing a second face, and an edge extending around the perimeter. A pulse generator and controller are coupled to three or more electrodes. Electrode arrangement facilitates selection of the particular electrodes that sense cardiac activity irrespective of one or more of positioning of the device, rotation of the housing, and which of the first and second faces of the housing is orientated toward the patient's skin. A first vector may be selected that provides for sensing cardiac activity, and a second vector may sense skeletal muscle activity. The vectors may be selected based on amplitude or signal-to-noise ratio exceeding a predetermined threshold. Methods may involve delivering defibrillation or cardioversion energy and/or determining cardiac rhythm states using selected vectors.

15 Claims, 13 Drawing Sheets

U.S. PATENT DOCUMENTS

| | | |
|---|---|---|
| 5,284,136 A | 2/1994 | Hauck et al. |
| 5,292,338 A | 3/1994 | Bardy |
| 5,299,118 A | 3/1994 | Martens et al. |
| 5,300,106 A | 4/1994 | Dahl et al. |
| 5,301,677 A | 4/1994 | Hsung |
| 5,313,953 A | 5/1994 | Yomtov et al. |
| 5,314,430 A | 5/1994 | Bardy |
| 5,314,459 A | 5/1994 | Swanson et al. |
| 5,318,597 A | 6/1994 | Hauck et al. |
| 5,331,966 A | 7/1994 | Bennet et al. |
| 5,334,222 A | 8/1994 | Salo et al. |
| 5,360,442 A | 11/1994 | Dahl et al. |
| 5,366,496 A | 11/1994 | Dahl et al. |
| 5,372,606 A | 12/1994 | Lang et al. |
| 5,376,103 A | 12/1994 | Anderson et al. |
| 5,376,106 A | 12/1994 | Stahmann et al. |
| 5,388,578 A | 2/1995 | Yomtov et al. |
| 5,391,200 A | 2/1995 | KenKnight et al. |
| 5,397,342 A | 3/1995 | Heil, Jr. et al. |
| 5,411,031 A | 5/1995 | Yomtov |
| 5,411,525 A | 5/1995 | Swanson et al. |
| 5,411,539 A | 5/1995 | Neisz |
| 5,439,482 A | 8/1995 | Adams et al. |
| 5,441,518 A | 8/1995 | Adams et al. |
| 5,466,245 A | 11/1995 | Spinelli et al. |
| 5,468,254 A | 11/1995 | Hahn et al. |
| 5,476,485 A | 12/1995 | Weinberg et al. |
| 5,483,969 A | 1/1996 | Testerman et al. |
| 5,520,176 A | 5/1996 | Cohen |
| 5,520,191 A | 5/1996 | Karlsson et al. |
| 5,522,862 A | 6/1996 | Testerman et al. |
| 5,531,779 A | 7/1996 | Dahl et al. |
| 5,545,186 A | 8/1996 | Olson et al. |
| 5,545,202 A | 8/1996 | Dahl et al. |
| 5,601,607 A | 2/1997 | Adams |
| 5,603,732 A | 2/1997 | Dahl et al. |
| 5,620,466 A | 4/1997 | Haefner et al. |
| 5,634,938 A | 6/1997 | Swanson et al. |
| 5,641,326 A | 6/1997 | Adams |
| 5,645,570 A | 7/1997 | Corbucci |
| 5,662,688 A | 9/1997 | Haefner et al. |
| 5,697,953 A | 12/1997 | Kroll et al. |
| 5,704,365 A | 1/1998 | Albrecht et al. |
| 5,713,355 A | 2/1998 | Richardson et al. |
| 5,713,933 A | 2/1998 | Condie et al. |
| 5,724,984 A | 3/1998 | Arnold et al. |
| 5,792,188 A | 8/1998 | Starkweather et al. |
| 5,802,188 A | 9/1998 | McDonough |
| 5,827,326 A | 10/1998 | Kroll et al. |
| 5,844,680 A | 12/1998 | Sperling |
| 5,855,593 A | 1/1999 | Olson et al. |
| 5,891,023 A | 4/1999 | Lynn |
| 5,895,414 A | 4/1999 | Sanchez-Zambrano |
| 5,902,250 A | 5/1999 | Verrier et al. |
| 5,911,218 A | 6/1999 | DiMarco |
| 5,916,243 A | 6/1999 | KenKnight et al. |
| 5,957,956 A | 9/1999 | Kroll et al. |
| 5,970,975 A | 10/1999 | Estes et al. |
| 5,981,011 A | 11/1999 | Overcash et al. |
| 5,987,352 A * | 11/1999 | Klein et al. ............ 600/509 |
| 5,997,526 A | 12/1999 | Giba et al. |
| 6,026,320 A | 2/2000 | Carlson et al. |
| 6,044,298 A | 3/2000 | Salo et al. |
| 6,055,454 A | 4/2000 | Heemels |
| 6,059,725 A | 5/2000 | Steinschneider |
| 6,091,986 A | 7/2000 | Keimel |
| 6,099,479 A | 8/2000 | Christopherson et al. |
| 6,115,628 A | 9/2000 | Stadler et al. |
| 6,141,581 A | 10/2000 | Olson et al. |
| 6,141,590 A | 10/2000 | Renirie et al. |
| 6,148,230 A | 11/2000 | KenKnight |
| 6,148,233 A | 11/2000 | Owen et al. |
| 6,200,265 B1 | 3/2001 | Walsh et al. |
| 6,205,357 B1 | 3/2001 | Ideker et al. |
| 6,221,011 B1 | 4/2001 | Bardy |
| 6,227,072 B1 | 5/2001 | Ritchey et al. |
| 6,240,316 B1 | 5/2001 | Richmond et al. |
| 6,259,947 B1 | 7/2001 | Olson et al. |
| 6,269,269 B1 | 7/2001 | Ottenhoff et al. |
| 6,270,457 B1 | 8/2001 | Bardy |
| 6,273,856 B1 | 8/2001 | Sun et al. |
| 6,275,727 B1 | 8/2001 | Hopper et al. |
| 6,277,072 B1 | 8/2001 | Bardy |
| 6,280,380 B1 | 8/2001 | Bardy |
| 6,280,462 B1 | 8/2001 | Hauser et al. |
| 6,285,907 B1 | 9/2001 | Kramer et al. |
| 6,312,378 B1 | 11/2001 | Bardy |
| 6,327,499 B1 | 12/2001 | Alt |
| 6,336,903 B1 | 1/2002 | Bardy |
| 6,351,670 B1 | 2/2002 | Kroll |
| 6,351,673 B1 | 2/2002 | Ding et al. |
| 6,358,203 B2 | 3/2002 | Bardy |
| 6,360,127 B1 | 3/2002 | Ding et al. |
| 6,361,494 B1 | 3/2002 | Lindenthaler |
| 6,368,284 B1 | 4/2002 | Bardy |
| 6,371,922 B1 | 4/2002 | Baumann et al. |
| 6,398,728 B1 | 6/2002 | Bardy |
| 6,405,085 B1 | 6/2002 | Graupner et al. |
| 6,409,675 B1 | 6/2002 | Turcott |
| 6,411,848 B2 | 6/2002 | Kramer et al. |
| 6,415,174 B1 | 7/2002 | Bebehani et al. |
| 6,424,865 B1 | 7/2002 | Ding |
| 6,438,407 B1 | 8/2002 | Ousdigian et al. |
| 6,438,410 B2 | 8/2002 | Hsu et al. |
| 6,440,066 B1 | 8/2002 | Bardy |
| 6,449,503 B1 | 9/2002 | Hsu |
| 6,459,929 B1 | 10/2002 | Hopper et al. |
| 6,463,325 B1 | 10/2002 | Bolz |
| 6,480,733 B1 | 11/2002 | Turcott |
| 6,487,443 B2 | 11/2002 | Olson et al. |
| 6,490,485 B1 | 12/2002 | Sun et al. |
| 6,491,639 B1 | 12/2002 | Turcott |
| 6,496,715 B1 * | 12/2002 | Lee et al. ............ 600/424 |
| 6,497,658 B2 | 12/2002 | Roizen et al. |
| 6,505,067 B1 | 1/2003 | Lee et al. |
| 6,512,940 B1 | 1/2003 | Brabec et al. |
| 6,522,915 B1 | 2/2003 | Ceballos et al. |
| 6,542,775 B2 | 4/2003 | Ding et al. |
| 6,564,106 B2 | 5/2003 | Guck et al. |
| 6,584,351 B1 | 6/2003 | Ekwall |
| 6,595,927 B2 | 7/2003 | Pitts-Crick et al. |
| 6,597,951 B2 | 7/2003 | Kramer et al. |
| 6,607,509 B2 | 8/2003 | Bobroff et al. |
| 6,615,083 B2 | 9/2003 | Kupper |
| 6,622,046 B2 | 9/2003 | Fraley et al. |
| 6,641,542 B2 | 11/2003 | Cho et al. |
| 6,699,200 B2 * | 3/2004 | Cao et al. ............ 600/508 |
| 6,731,984 B2 | 5/2004 | Cho et al. |
| 6,752,765 B1 | 6/2004 | Jensen et al. |
| 6,752,766 B2 | 6/2004 | Kowallik et al. |
| 6,754,528 B2 | 6/2004 | Bardy et al. |
| 6,760,615 B2 | 7/2004 | Ferek-Petric |
| 6,766,190 B2 | 7/2004 | Ferek Petric |
| 6,773,404 B2 | 8/2004 | Poezevera et al. |
| 6,778,860 B2 | 8/2004 | Ostroff et al. |
| 6,786,866 B2 | 9/2004 | Odagiri et al. |
| 6,788,974 B2 | 9/2004 | Bardy et al. |
| 6,810,287 B2 | 10/2004 | Zhu et al. |
| 6,823,214 B1 | 11/2004 | Sun et al. |
| 6,834,204 B2 | 12/2004 | Ostroff et al. |
| 6,839,593 B1 | 1/2005 | Sun et al. |
| 6,856,835 B2 | 2/2005 | Bardy et al. |
| 6,865,417 B2 | 3/2005 | Rissmann et al. |
| 6,866,044 B2 | 3/2005 | Bardy et al. |
| 6,884,218 B2 | 4/2005 | Olson |
| 6,904,320 B2 | 6/2005 | Park et al. |
| 6,912,419 B2 | 6/2005 | Hill et al. |
| 6,927,721 B2 | 8/2005 | Ostroff |
| 6,928,324 B2 | 8/2005 | Park et al. |
| 6,944,579 B2 | 9/2005 | Shimizu |
| 6,950,705 B2 | 9/2005 | Bardy et al. |
| 6,952,608 B2 | 10/2005 | Ostroff |
| 6,952,610 B2 | 10/2005 | Ostroff et al. |
| 6,954,670 B2 | 10/2005 | Ostroff |
| 6,959,214 B2 | 10/2005 | Pape et al. |
| 6,961,619 B2 | 11/2005 | Casey |
| 6,983,264 B2 | 1/2006 | Shimizu |

| | | | |
|---|---|---|---|
| 6,988,003 B2 | 1/2006 | Bardy et al. | |
| 6,988,498 B2 | 1/2006 | Berthon-Jones et al. | |
| 6,993,389 B2 | 1/2006 | Ding et al. | |
| 6,999,817 B2 | 2/2006 | Park et al. | |
| 7,016,730 B2 | 3/2006 | Ternes | |
| 7,025,730 B2 | 4/2006 | Cho et al. | |
| 7,027,861 B2 | 4/2006 | Thompson | |
| 7,027,871 B2 | 4/2006 | Burnes et al. | |
| 7,039,459 B2 | 5/2006 | Bardy et al. | |
| 7,039,465 B2 | 5/2006 | Bardy et al. | |
| 7,043,299 B2 | 5/2006 | Erlinger et al. | |
| 7,050,851 B2 | 5/2006 | Plombon et al. | |
| 7,065,407 B2 | 6/2006 | Bardy et al. | |
| 7,069,080 B2 | 6/2006 | Bardy et al. | |
| 7,076,296 B2 | 7/2006 | Rissmann et al. | |
| 7,090,682 B2 | 8/2006 | Sanders et al. | |
| 7,092,754 B2 | 8/2006 | Bardy et al. | |
| 7,092,755 B2 | 8/2006 | Florio | |
| 7,117,036 B2 | 10/2006 | Florio | |
| 7,120,495 B2 | 10/2006 | Bardy et al. | |
| 7,123,960 B2 | 10/2006 | Ding et al. | |
| 7,127,290 B2 | 10/2006 | Girouard et al. | |
| 7,146,212 B2 | 12/2006 | Bardy et al. | |
| 7,149,575 B2 | 12/2006 | Ostroff et al. | |
| 7,181,285 B2 | 2/2007 | Lindh et al. | |
| 7,194,302 B2 | 3/2007 | Bardy et al. | |
| 7,194,309 B2 | 3/2007 | Ostroff et al. | |
| 7,206,635 B2 | 4/2007 | Cho et al. | |
| 7,212,862 B2 | 5/2007 | Park et al | |
| 7,215,890 B2 | 5/2007 | Tegge, Jr. et al. | |
| 7,245,962 B2 | 7/2007 | Ciaccio et al. | |
| 7,252,640 B2 | 8/2007 | Ni et al. | |
| 7,260,432 B2 | 8/2007 | Kramer et al. | |
| 7,263,399 B2 | 8/2007 | Carlsom | |
| 7,308,311 B2 | 12/2007 | Sorensen et al. | |
| 7,396,333 B2 | 7/2008 | Stahmann et al. | |
| 7,428,468 B2 | 9/2008 | Takemura et al. | |
| 7,499,750 B2 | 3/2009 | Haefner et al. | |
| 7,720,541 B2 | 5/2010 | Stahmann et al. | |
| 7,766,842 B2 | 8/2010 | Ni et al. | |
| 2001/0034487 A1* | 10/2001 | Cao et al. | 600/508 |
| 2002/0035377 A1 | 3/2002 | Bardy et al. | |
| 2002/0035378 A1 | 3/2002 | Bardy et al. | |
| 2002/0035379 A1 | 3/2002 | Bardy et al. | |
| 2002/0035381 A1 | 3/2002 | Bardy et al. | |
| 2002/0052636 A1 | 5/2002 | Bardy et al. | |
| 2002/0082658 A1 | 6/2002 | Heinrich et al. | |
| 2002/0095184 A1 | 7/2002 | Bardy et al. | |
| 2002/0107544 A1 | 8/2002 | Ostroff et al. | |
| 2002/0107545 A1 | 8/2002 | Rissmann et al. | |
| 2002/0107549 A1 | 8/2002 | Bardy et al. | |
| 2003/0023175 A1 | 1/2003 | Arzbaecher et al. | |
| 2003/0212436 A1 | 11/2003 | Brown | |
| 2003/0216789 A1 | 11/2003 | Deem et al. | |
| 2004/0230230 A1 | 11/2004 | Lindstrom | |
| 2004/0230243 A1* | 11/2004 | Haefner et al. | 607/27 |
| 2005/0042589 A1 | 2/2005 | Hatlestad et al. | |
| 2005/0288600 A1* | 12/2005 | Zhang et al. | 600/510 |
| 2006/0069322 A1* | 3/2006 | Zhang et al. | 600/512 |
| 2007/0161873 A1 | 7/2007 | Ni et al. | |

FOREIGN PATENT DOCUMENTS

| | | |
|---|---|---|
| EP | 0770407 | 5/1997 |
| EP | 1038498 | 9/2000 |
| EP | 1162125 | 12/2001 |
| EP | 1172125 | 1/2002 |
| EP | 1317943 | 6/2003 |
| WO | WO8402080 | 7/1984 |
| WO | WO9203983 | 3/1992 |
| WO | WO9217240 | 10/1992 |
| WO | WO9220402 | 11/1992 |
| WO | WO9904841 | 4/1999 |
| WO | WO03003905 | 1/2003 |

OTHER PUBLICATIONS

Belouchrani et al., Blind Source Separation Based on Time-Frequency Signal Representations, IEEE Transactions on Signal Processing, vol. 46, No. 11, pp. 2888-2897, Nov. 1998.

Bradley et al., Pathophysiologic and Therapeutic Implications of Sleep Apnea in Congestive Heart Failure, 3 J. Cardiac Failure 223-240, 1996, Abstract only.

Comon, Independent component analysis, A new concept?, Signal Processing, vol. 36, No. 3, pp. 287-314, Apr. 1994.

Gallois et al., Multi-Channel Analysis of the EEG Signals and Statistic Particularities for Epileptic Seizure Forecast, Second Joint EMBS/BMES Conference, pp. 208-215, Oct. 23-26, 2002.

Gradaus et al., Nonthoracotomy Implantable Cardioverter Defibrillator Placement in Children: Use of a Subcutaneous Array Leads and Abdominally Placed Implantable Cardioverter Defibrillators in Children, J. of Cardiovascular Electrophysiology, vol. 12, No. 3, pp. 356-360, Mar. 2001.

Garrigue et al., Benefit of Atrial Pacing in Sleep Apnea Syndrome, 346 N. Engl. J. Med. 404-412, 2002, 9 pages.

Garrigue et al., Night Atrial Overdrive with DDD Pacing Results in a Significant Reduction of Sleep Apnea Episodes and QOL Improvement in Heart Failure Patients, NASPE, 2001, Abstract only.

Garrigue et al., Night Atrial Overdrive with DDD Pacing: A New Therapy for Sleep Apnea Syndrome, NASPE, 2000, Abstract only.

Hartz et al., New Approach to Defibrillator Insertion, J. Thoracic Cardiovascular Surgery, vol. 97, pp. 920-922, 1989, 3 pages.

Hilton et al., Evaluation of Frequency and Time-frequency Spectral Analysis of Heart Rate Variability as a Diagnostic Marker of the Sleep Apnea Syndrome, 37 Med. Biol. Eng. Comput. 760-769, 1999.

Javaheri, A Mechanism of Central Sleep Apnea in Patients With Heart Failure, 341 N. Engl. J. Med. 949-954, 1999, 6 pages.

Javaheri et al., Sleep Apnea in 81 Ambulatory Male Patients with Stable Heart Failure: Types and Their Prevalences, Consequences, and Presentations, 97 Circulation 2154-2159, 1998.

Kolettis, MD, PhD et al., Submammary Implantation of a Cardioverter-Defibrillator with a Nonthoracotomy Lead System, Am. Heart J., vol. 126, pp. 1222-1223, Nov. 1993.

Krahn et al., Recurrent syncope. Experience with an implantable loop record. Cardiol. Clin., vol. 15(2), May 1997, pp. 316-326.

Leng et al., Lead Configuration for Defibrillator Implantation in a Patient with Congenital Heart Disease and a Mechanical Prosthetic Tricuspid Valve, PACE, vol. 24, No. 8, pp. 1291-1292 (Aug. 2001).

Mettauer et al. VO2 kinetics reveal a central limitation at the onset of subthreshold exercise in heart transplant recipients, J. Appl. Physiol 88:1228-1238, 2000, downloaded from jap.physiology.org on Jul. 28, 2008.

Park et al., Use of an Implantable Cardioverter Defibrillator in an Eight-Month-Old Infant with Ventricular Fibrillation Arising from a Myocardial Fibroma, PACE, vol. 22, No. 1, pp. 138-139, Jan. 1999.

Rieta, et al., Atrial Activity Extraction Based on Blind Source Separation as an Alternative to QRST Cancellation for Atrial Fibrillation Analysis, Computers in Cardiology, vol. 27, pp. 69-72, 2000.

Roche et al., Screening of Obstructive Sleep Apnea Syndrome by Heart Rate Variability Analysis, 100 Circulation 1411-1455, 1999.

Schuder et al., Experimental Ventricular Defibrillation with an Automatic and Completely Implanted System, Trans. Am. Soc. Artif. Int. Organs, vol. 16, pp. 207-212, 1970.

Schuder et al., Transthoracic Ventricular Defibrillation in the Dog with Truncated and Untruncated Exponential Stimuli, IEEE Trans. On Bio-Medical Engin, vol. BME-18, No. 6, pp. 410-415, Nov. 1971.

Schuder et al., Ventricular Defibrillation in the Dog Using Implanted and Partially Implanted Electrode Systems, Am. J. of Cardiology, vol. 33, pp. 243-247, Feb. 1974.

Smits et al., Defibrillation Threshold (DFT) Model of a Fully Subcutaneous ICD System, Europace Supplements, vol. 2, Jun. 2001 at col. 778, p. B83.

Stirbis et al., Optmizing the Shape of Implanted Artificial Pacemakers, Kaunas Medical Institute. Translated from Meditsinskaya Tekhnika, No. 6, pp. 25-27, 1986.

Young et al., The Occurrence of Sleep-Disordered Breathing Among Middle Aged Adults, N. Engl. J. Med. 1230-1235, 1993.

Zarzoso et al., Blind Separation of Independent Sources for Virtually Any Source Probability Density Function, IEEE Transactions on Signal Processing, vol. 47, No. 9, pp. 2419-2432, Sep. 1999.

Zarzoso et al., Noninvasive Fetal Electrocardiogram Extraction: Blind Separation Versus Adaptive Noise Cancellation, IEEE Transactions on Biomedical Engineering, vol. 48, No. 1, pp. 12-18, Jan. 2001.

File history for U.S. Appl. No. 10/738,608, as retrieved from USPTO PAIR system on Jan. 12, 2011, 284 pages.

* cited by examiner

POSITIONALLY ADAPTABLE IMPLANTABLE CARDIAC DEVICE

FIELD OF THE INVENTION

The present invention relates generally to implantable medical devices and, more particularly, to cardiac sensing and/or stimulation devices that are adaptable to implant location and positioning.

BACKGROUND OF THE INVENTION

The healthy heart produces regular, synchronized contractions. Rhythmic contractions of the heart are normally controlled by the sinoatrial (SA) node, which is a group of specialized cells located in the upper right atrium. The SA node is the normal pacemaker of the heart, typically initiating 60-100 heartbeats per minute. When the SA node is pacing the heart normally, the heart is said to be in normal sinus rhythm.

If the heart's electrical activity becomes uncoordinated or irregular, the heart is denoted to be arrhythmic. Cardiac arrhythmia impairs cardiac efficiency and may be a potential life-threatening event. Cardiac arrhythmias have a number of etiological sources, including tissue damage due to myocardial infarction, infection, or degradation of the heart's ability to generate or synchronize the electrical impulses that coordinate contractions.

Bradycardia occurs when the heart rhythm is too slow. This condition may be caused, for example, by impaired function of the SA node, denoted sick sinus syndrome, or by delayed propagation or blockage of the electrical impulse between the atria and ventricles. Bradycardia produces a heart rate that is too slow to maintain adequate circulation.

When the heart rate is too rapid, the condition is denoted tachycardia. Tachycardia may have its origin in either the atria or the ventricles. Tachycardias occurring in the atria of the heart, for example, include atrial fibrillation and atrial flutter. Both conditions are characterized by rapid contractions of the atria. Besides being hemodynamically inefficient, the rapid contractions of the atria may also adversely affect the ventricular rate.

Ventricular tachycardia occurs, for example, when electrical activity arises in the ventricular myocardium at a rate more rapid than the normal sinus rhythm. Ventricular tachycardia may quickly degenerate into ventricular fibrillation. Ventricular fibrillation is a condition denoted by extremely rapid, uncoordinated electrical activity within the ventricular tissue. The rapid and erratic excitation of the ventricular tissue prevents synchronized contractions and impairs the heart's ability to effectively pump blood to the body, which may be a fatal condition unless the heart is returned to sinus rhythm within a few minutes.

Implantable cardiac rhythm management systems have been used as an effective treatment for patients with serious arrhythmias. These systems typically include one or more leads and circuitry to sense signals from one or more interior and/or exterior surfaces of the heart. Such systems also include circuitry for generating electrical pulses that are applied to cardiac tissue at one or more interior and/or exterior surfaces of the heart. For example, leads extending into the patient's heart are connected to electrodes that contact the myocardium for sensing the heart's electrical signals and for delivering pulses to the heart in accordance with various therapies for treating arrhythmias.

Typical Implantable cardioverter/defibrillators (ICDs) include one or more endocardial leads to which at least one defibrillation electrode is connected. Such ICDs are capable of delivering high-energy shocks to the heart, interrupting the ventricular tachyarrhythmia or ventricular fibrillation, and allowing the heart to resume normal sinus rhythm. ICDs may also include pacing functionality.

SUMMARY OF THE INVENTION

The present invention is directed to cardiac monitoring and/or stimulation methods and systems that provide monitoring, defibrillation therapies, pacing therapies, or a combination of these capabilities. Embodiments of the present invention relate generally to cardiac sensing and/or stimulation devices that are adaptable to implant location and positioning, and embodiments that employ automated vector selection from multiple electrodes.

Embodiments of implantable cardiac devices in accordance with the present invention include a housing having a first face opposing a second face, and an edge extending from a perimeter of the first face to a perimeter of the second face. A pulse generator with a controller is provided in the housing. Three or more electrodes are coupled to the pulse generator and arranged in a spaced relationship in or on the housing. The arrangement of the electrodes facilitates controller selection of particular electrodes that provide for sensing of cardiac activity irrespective of positional orientation of the housing within a patient. The arrangement of the electrodes may also facilitate controller selection of the particular electrodes that provide for sensing of cardiac activity irrespective of changes in positional orientation of the housing within the patient.

The controller may select particular electrodes that provide for sensing of cardiac activity irrespective of rotation of the housing within the patient. The arrangement of the plurality of electrodes may also facilitate controller selection of the particular electrodes that provide for sensing of cardiac activity irrespective of which of the first and second faces of the housing is orientated toward the patient's skin. In another embodiment, the arrangement of the plurality of electrodes facilitates controller selection of the particular electrodes that provide for sensing of cardiac activity irrespective of both of rotation of the housing within the patient and which of the first and second faces of the housing is orientated toward the patient's skin.

The arrangement of the plurality of electrodes may facilitate controller selection of a first set of electrodes that preferentially provide for sensing of cardiac activity and a second set of electrodes that preferentially provide for sensing of skeletal muscle activity. The controller may select the particular electrodes that provide for sensing a cardiac signal having an amplitude or signal-to-noise ratio that exceeds a predetermined threshold. The pulse generator may be configured to deliver defibrillation or cardioversion energy.

The electrodes may include at least three electrodes positioned on the edge of the housing and wrapping over a portion of the first and second faces of the housing. In another embodiment the electrodes include at least three electrodes positioned on the first face of the housing and at least three electrodes positioned on the second face of the housing. The controller may be configured to determine cardiac rhythm states using selected electrodes.

Methods of sensing cardiac activity in accordance with embodiments of the present invention involve providing an implantable housing that supports a plurality of electrodes arranged in a spaced relationship, the housing and electrodes configured for subcutaneous, non-intrathoracic placement in a patient. The electrodes are selectively combinable to define two or more sense vectors. One sense vector may be selected for sensing cardiac activity. A vector may be selected to facilitate sensing of cardiac activity irrespective of positional orientation of the housing within the patient.

The selected sense vector or selecting another of the plurality of sense vectors facilitates sensing of cardiac activity irrespective of changes in positional orientation and/or rotation of the housing within a patient. Further embodiments select vectors useful for sensing of cardiac activity irrespective of which of a first face and a second face of the housing is orientated toward the patient's skin. Further embodiments select vectors useful for sensing of cardiac activity irrespective of both of rotation of the housing within the patient and which of a first face and a second face of the housing is orientated toward the patient's skin.

Other embodiments involve selecting a first sense vector that preferentially provides for sensing of cardiac activity and a second sense vector that preferentially provides for sensing of skeletal muscle activity. The vector or vectors may be selected based on an amplitude or signal-to-noise ratio that exceeds a predetermined threshold. Methods may further involve delivering defibrillation or cardioversion energy to the patient's heart in response to detecting a cardiac condition requiring delivery of defibrillation or cardioversion energy, or determining cardiac rhythm states using selected ones of the plurality of sense vectors.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
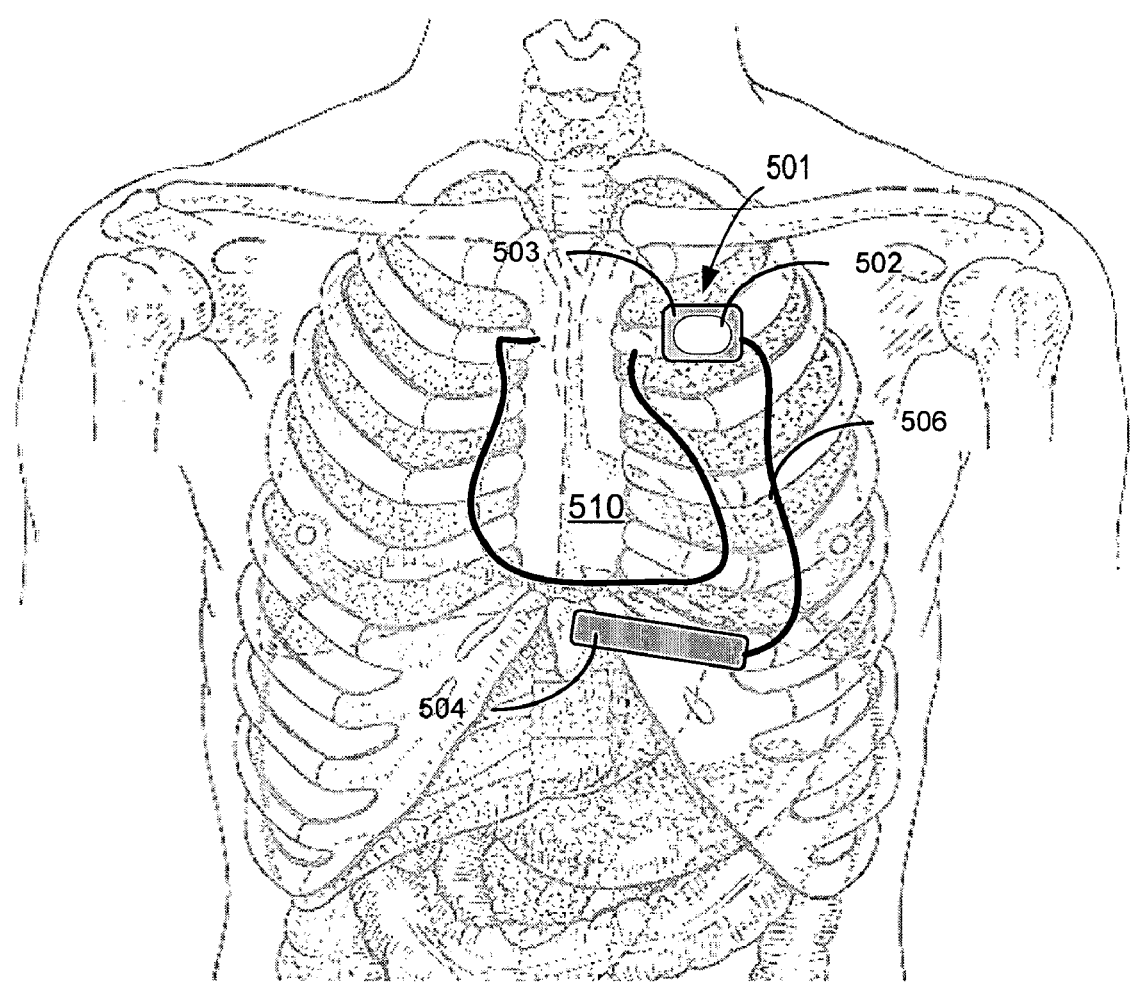
FIG. 1 is a diagram illustrating components of a cardiac sensing and/or stimulation device positionally and orientationally adaptable in accordance with an embodiment of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

An implanted device according to the present invention may include one or more of the features, structures, methods, or combinations thereof described hereinbelow. For example, a cardiac monitor or a cardiac stimulator may be implemented to include one or more of the advantageous features and/or processes described below. It is intended that such a monitor, stimulator, or other implanted or partially implanted device need not include all of the features described herein, but may be implemented to include selected features that provide for unique structures and/or functionality. Such a device may be implemented to provide a variety of therapeutic or diagnostic functions.

Methods and devices in accordance with the present invention provide multiple electrodes in or on an implantable device that allow a physician freedom of device orientation during implantation. Electrodes may reside on both the top and bottom and/or wrap around the sides of an implantable device to reduce the sensing and detection variability due to implantation techniques concerning which side of an implantable device faces the skin. Multiple electrodes used in combination with vector selection methodologies of the present invention also reduce the chances of sensing and detection variability due to implantation techniques concerning rotation of the device and/or positioning of the device. Methods and devices in accordance with the present invention provide the physician with the ability to implant a device without concern to device orientation at implant.

In general terms, cardiac sensing and/or stimulation devices that are adaptable to implant location and positioning in accordance with the present invention may be used to monitor and/or treat cardiac function in a patient. One such device is an implantable cardiac sensing and/or stimulation (ITCS) device that may be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy. It is understood that elements of the ITCS device may be located at several different body locations, such as in the chest, abdominal, or subclavian region with electrode elements respectively positioned at different regions near, around, in, or on the heart.

The primary housing (e.g., the active or non-active can) of the ITCS device, for example, may be configured for positioning outside of the rib cage at an intercostal or subcostal location, within the abdomen, or in the upper chest region (e.g., subclavian location, such as above the third rib). In one configuration, as is illustrated in FIG. 1, electrode subsystems of an ITCS system are arranged about a patient's heart 510. The ITCS system includes a first electrode subsystem, comprising a can top electrode assembly 502 on a top face 503 of a can 501. An electrode assembly (not shown) is also provided on a bottom face of the can 501, as will be further illustrated and discussed below. An optional electrode assembly 504 is also illustrated in FIG. 1 that may include one or more of electrodes, sensors, and multi-element electrodes. The optional electrode assembly 504 is coupled to the can 501 using a lead 506.

In various configurations, the optional electrode subsystem 504 may include a combination of electrodes. The combination of electrodes of the optional electrode subsystem 504 may include coil electrodes, tip electrodes, ring electrodes, multi-element coils, spiral coils, spiral coils mounted on non-conductive backing, screen patch electrodes, and other electrode configurations as will be described below. A suitable non-conductive backing material is silicone rubber, for example.

In accordance with one embodiment, the housing 501 may resemble that of a conventional implantable ICD, is approximately 20-100 cc in volume, with a thickness of 0.4 to 2 cm and with a surface area on each face of approximately 30 to 100 cm$^2$. As previously discussed, portions of the housing may be electrically isolated from tissue to optimally direct current flow. For example, portions of the housing 501 may be covered with a non-conductive, or otherwise electrically resistive, material to direct current flow. Suitable non-conductive material coatings include those formed from silicone rubber, polyurethane, or parylene, for example.

In addition, or alternatively, all or portions of the housing 501 may be treated to change the electrical conductivity characteristics thereof for purposes of optimally directing current flow. Various known techniques may be employed to modify the surface conductivity characteristics of the housing 501, such as by increasing or decreasing surface conductivity, to optimize current flow. Such techniques may include those that mechanically or chemically alter the surface of the housing 501 to achieve desired electrical conductivity characteristics.

An ITCS device in accordance with embodiments of the present invention includes two or more electrodes on both the top face and bottom face of the can 501. Various matching of electrodes may be used for sensing and/or stimulating the heart 510. Every pair combination of electrodes has a corresponding vector for sensing and/or stimulation. Spatially diverse electrodes can, for example, include sets of electrodes arranged in an orthogonal relationship to one another, it being understood that other non-orthogonal relationships can be employed.

For each spatially diverse set of electrodes, a primary pair of electrodes may be selected based on, for example, the largest content of cardiac signal. The corresponding spatially diverse electrodes would then be selected for the purpose of sensing and/or stimulating the heart 510. Examples of spatially diverse electrodes and electrode arrays are further described in commonly owned U.S. Pat. No. 7,499,750, which is hereby incorporated herein by reference.

Cardiac sensing and/or stimulation devices that are adaptable to implant location and positioning in accordance with the present invention may be adapted to their implant environment manually, such as by a clinician after implantation, or may be adapted to automatically configure themselves. An ITCS device that implements an automated vector selection and orientation approach consistent with the present invention provides for automatically defining vectors useful for cardiac sensing and/or stimulation. Electrode arrays and/or multiple electrodes provide for many possible vectors useful for sensing cardiac activity, patient activity, and other signals useful for ITCS devices.

Figure 2A:
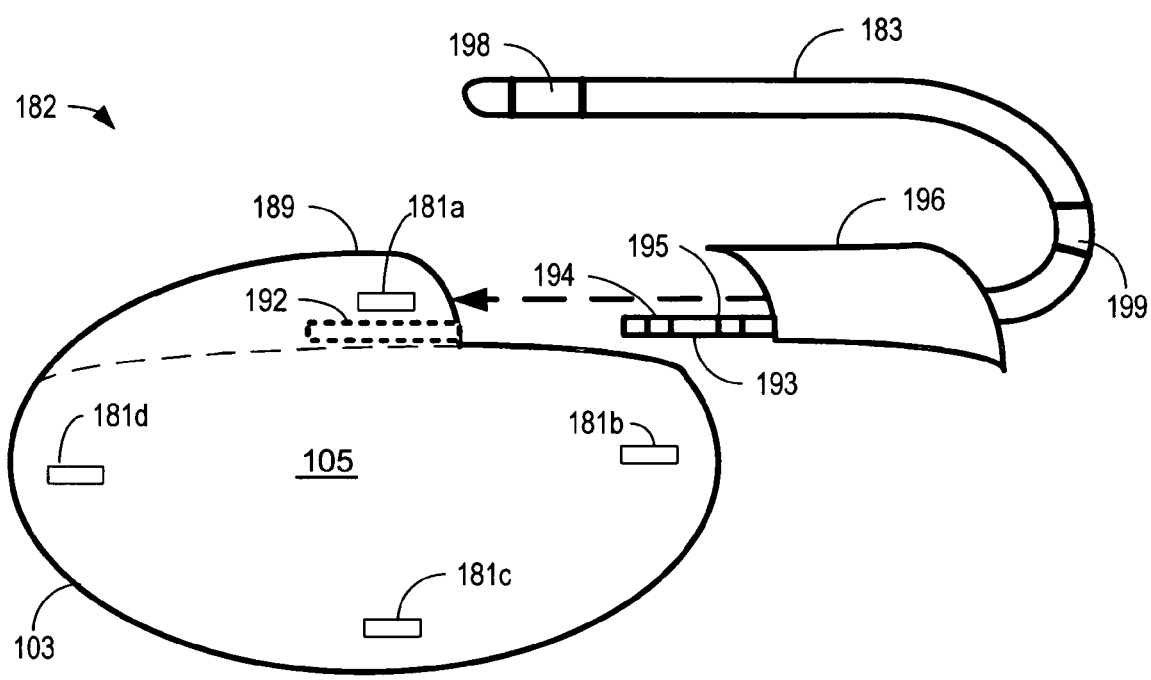
FIG. 2A is a top view of a positionally and orientationally adaptable ITCS device in accordance with the present invention.
Figure 2B:
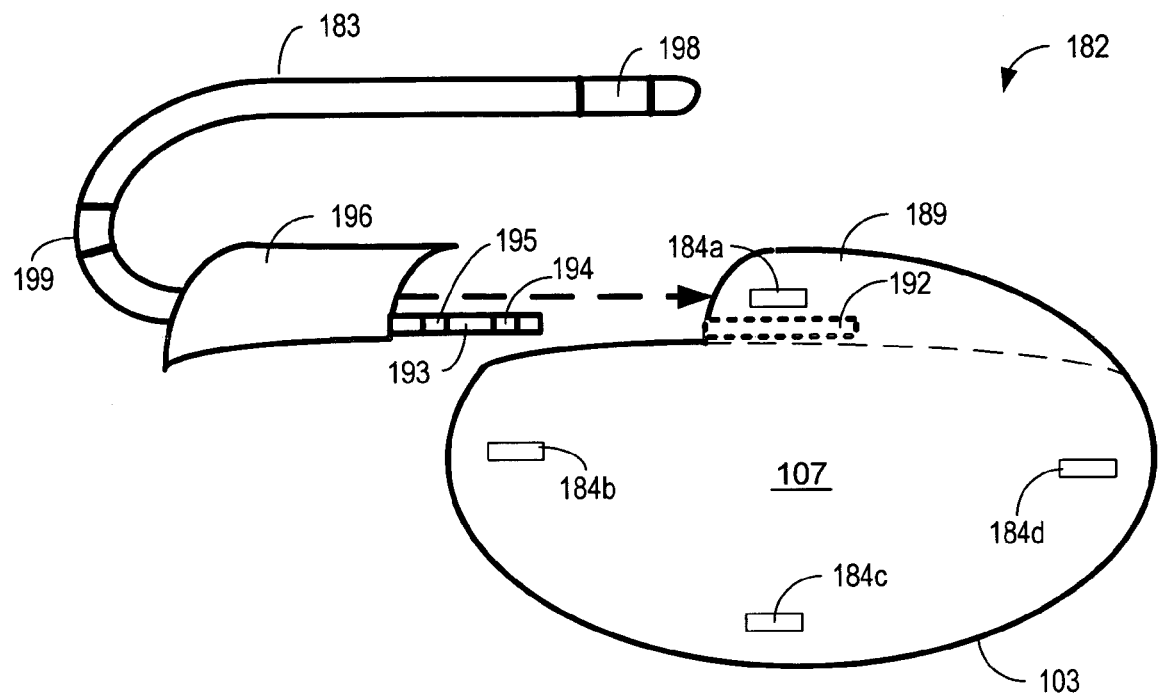
FIG. 2B is a bottom view of a positionally and orientationally adaptable ITCS device in accordance with the present invention.

FIGS. 2A and 2B are top and bottom views respectively of an ITCS device 182 in accordance with the present invention, having at least two electrodes on each face of a can 103. The ITCS device 182 may also include a first electrode 198 and a second electrode 199 coupled to the can 103 through a header 189, via an electrode module 196. The first electrode 198 and second electrode 199 may be located on a lead 183 (single or multiple lead, or electrode array), or may be located directly in or on the electrode module 196.

The can 103 is illustrated as incorporating the header 189. The header 189 may be configured to facilitate removable attachment between an electrode module 196 and the can 103, as is shown in the embodiment depicted in FIGS. 2A and 2B. The header 189 includes a female coupler 192 configured to accept a male coupler 193 from the electrode module 196. The male coupler 193 is shown having two electrode contacts 194, 195 for coupling one or more electrodes 197 through the electrode module 196 to the can 103. An electrode 181a is illustrated on the header 189 of the can 103. The can 103 is illustrated in FIGS. 2A and 2B having electrodes 181b, 181c, and 181d positioned on a top face 105 of the can 103 (FIG. 2A) and electrodes 184b, 184c, and 184d positioned on a bottom face 107 of the can 103 (FIG. 2B). The terms top and bottom are used for descriptive purposes only, and not as limitations to positioning.

According to one configuration of an orientation insensitive device in accordance with the present invention, a cardiac monitoring and/or stimulation device may be configured to include a pulse generator having a controller coupled to the electrodes 181a, 181b, 181c, 181d, 184a, 184b, 184c, and 184d. Electrode pairs and the cardiac signals from these electrode pairs may be used to compute the component of the cardiac activation vector for each pair. A first combination of electrodes may be determined useful to preferentially sense cardiac signals. The controller may select combinations of the multiple electrodes, and may sense a cardiac signal component for each combination, and choose the combination having the greatest magnitude cardiac signal as the combination useful for operation.

In accordance with a scanning methodology, combinations of the electrodes 181a, 181b, 181c, 181d, 184a, 184b, 184c, and 184d are selected, and cardiac signal components of signals acquired by each of the selected electrode combinations are sensed. Selecting the oriented sensing vector may involve selecting a combination of electrodes that provides a cardiac signal response that exceeds a threshold and/or provides the largest magnitude cardiac signal, for example.

In this and other configurations, the header 189 incorporates interface features (e.g., electrical connectors, ports, engagement features, and the like) that facilitate electrical connectivity with one or more lead and/or sensor systems, lead and/or sensor modules, and electrodes. The interface features of the header 189 may be protected from body fluids using known techniques.

The ITCS device 182 may further include one or more sensors in or on the can 103, header 189, electrode module 196, or lead(s) that couple to the header 189 or electrode module 196. Useful sensors may include electrophysiologic and non-electrophysiologic sensors, such as an acoustic sensor, an impedance sensor, a blood sensor, such as an oxygen saturation sensor (oximeter or plethysmographic sensor), a blood pressure sensor, minute ventilation sensor, or other sensors described or incorporated herein.

Figure 2C:
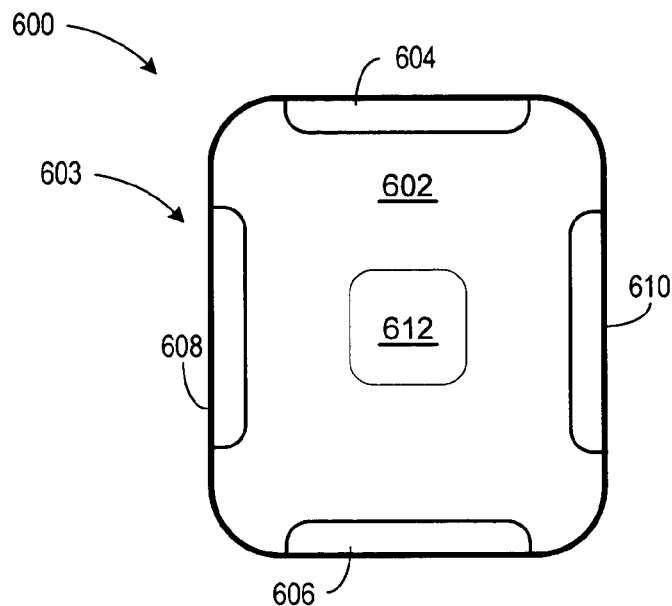
FIG. 2C is a top view of a positionally and orientationally adaptable ITCS device having side wrap-around electrodes in accordance with embodiments of the present invention.
Figure 2D:
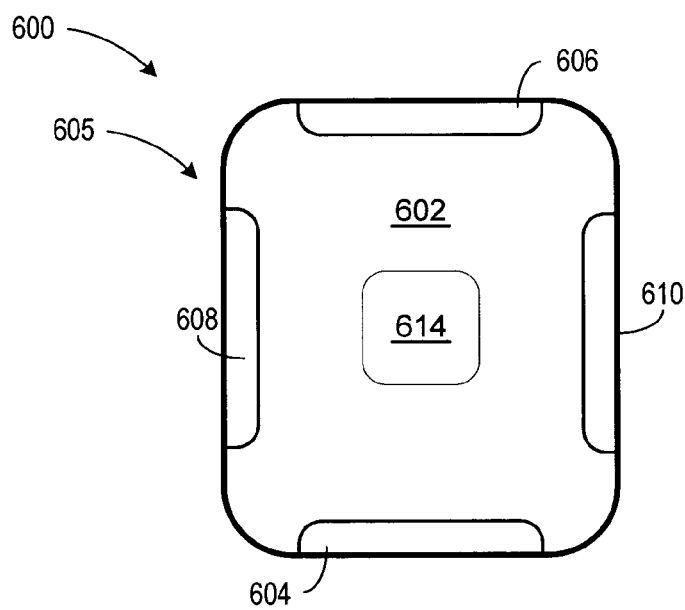
FIG. 2D is a bottom view of a positionally and orientationally adaptable ITCS device having side wrap-around electrodes in accordance with the embodiment illustrated in FIG. 2C.
Figure 2E:
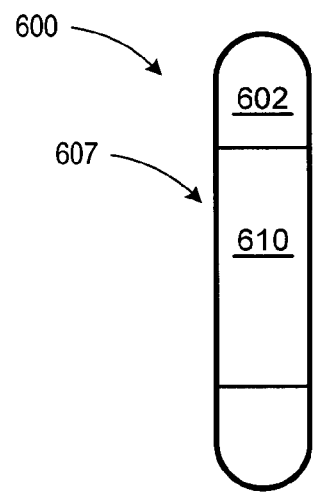
FIG. 2E is a side view of a positionally and orientationally adaptable ITCS device having side wrap-around electrodes in accordance with the embodiment illustrated in FIG. 2C.

FIGS. 2C, 2D, and 2E are top, bottom, and side views respectively of a positionally and orientationally adaptable ITCS device 600 having side wrap-around electrodes in accordance with embodiments of the present invention. Although the ITCS device 600 is illustrated as generally square in shape, the ITCS device 600 may be generally round, generally oval, generally triangular, generally square, generally pentagonal, generally hexagonal, or other shape without departing from the scope of the present invention.

The ITCS device 600 includes a housing 602 that may house the componentry generally associated with an ICD or other ITCS. The ITCS device 600 includes a top face 603 (FIG. 2C), a bottom face 605 (FIG. 2D), and at least one side 607 (FIG. 2E). The ITCS is illustrated as having multiple wrap-around electrodes, which wrap from the front, around the side, and onto the back of the ITCS device 600. An example of one type of wrap-around electrode is an electrode 610, which is illustrated as wrapping from the top face 603 in FIG. 2C, around the side 607 in FIG. 2E, and on the bottom face 605 in FIG. 2D.

Similarly, electrodes 604, 606, and 608 are illustrated in FIGS. 2C and 2D wrapping from the top face 603 to the bottom face 605. As stated previously, the terms top and bottom are intended as useful descriptors for illustrative purposes, and not intended to limit the actual use or orientation of the ITCS device 600. In addition to the electrodes 604, 606, 608, and 610, a top face electrode 612 is illustrated on the top face 603 in FIG. 2C, and a bottom face electrode 614 is illustrated on the bottom face 605 in FIG. 2D. Any of the electrodes illustrated in FIGS. 2C, 2D, and 2E may be used in any combination in accordance with the present invention to provide an implantation orientation insensitive ITCS device 600. For example, Electrodes 608 and 612 on the top face 603 may be associated with a skeletal muscle detection vector, and electrodes 608 and 614 on the bottom face 605 may be associated with the cardiac signal sense vector if the ITCS device 600 is implanted in a patient with the bottom face 605 facing the patient's skin and the top face 603 facing the patient's heart.

Figure 2F:
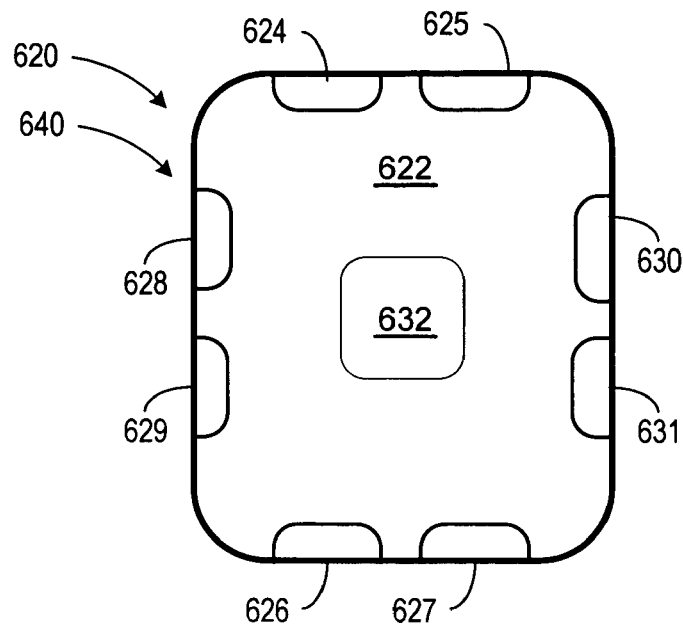
FIG. 2F is a top view of a positionally and orientationally adaptable ITCS device having side wrap-around electrodes in accordance with another embodiment of the present invention.
Figure 2G:
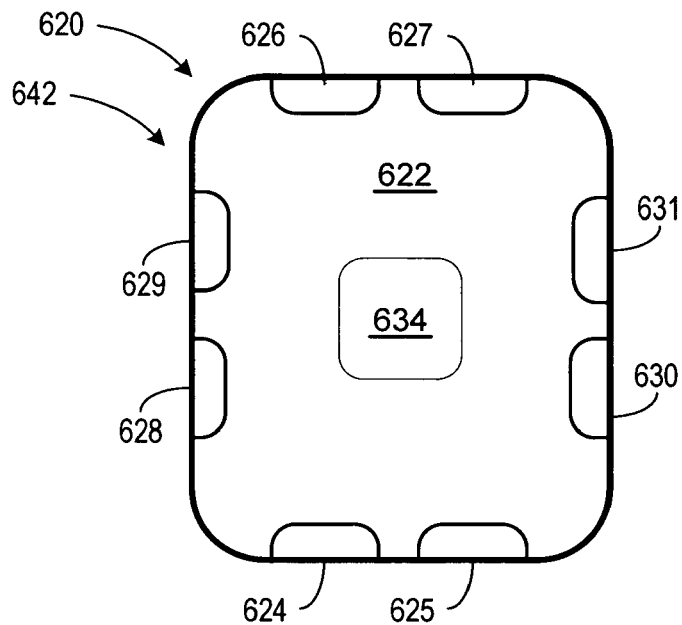
FIG. 2G is a bottom view of a positionally and orientationally adaptable ITCS device having side wrap-around electrodes in accordance with the embodiment illustrated in FIG. 2F.
Figure 2H:
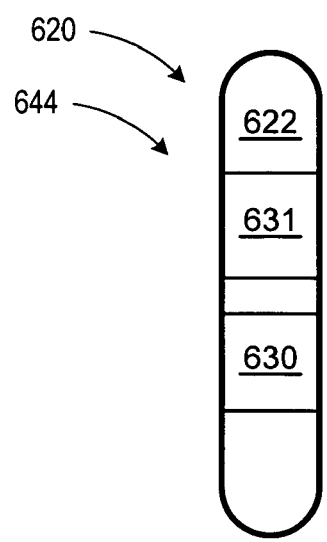
FIG. 2H is a side view of a positionally and orientationally adaptable ITCS device having side wrap-around electrodes in accordance with the embodiment illustrated in FIG. 2F.

FIGS. 2F, 2G, and 2H are top, bottom, and side views respectively of a positionally and orientationally adaptable ITCS device 620 having side wrap-around electrodes in accordance with another embodiment of the present invention. The ITCS device 620 includes a housing 622 that may house the componentry generally associated with an ICD or other ITCS. The ITCS device 620 includes a top face 640 (FIG. 2F), a bottom face 642 (FIG. 2G), and at least one side 644 (FIG. 2H). The ITCS device 620 is illustrated as having multiple wrap-around electrodes, which wrap from the front, around the side, and onto the back of the ITCS device 620. Examples of one type of wrap-around electrodes are an electrode 630 and an electrode 631, which are illustrated as wrapping from the top face 640 in FIG. 2F, around the side 644 in FIG. 2H, and on the bottom face 642 in FIG. 2G.

Similarly, electrodes 624, 625, 626, 627, 628, and 629 are illustrated in FIGS. 2F and 2G wrapping from the top face 640 to the bottom face 642. In addition to the electrodes 624, 625, 626, 627, 628, and 629, a top face electrode 632 is illustrated on the top face 640 in FIG. 2F, and a bottom face electrode 634 is illustrated on the bottom face 642 in FIG. 2G. Any of the electrodes illustrated in FIGS. 2F, 2G, and 2H may be used in any combination in accordance with the present invention to provide an implantation orientation insensitive ITCS device 620.

Methods in accordance with the present invention may further involve reducing a noise component of cardiac activity signals using noise signals, such as by linearly combining cardiac activity signals with the noise signals to reduce a noise component of the cardiac activity signals. Methods and devices using linear combinations of signals to reduce noise and/or separate signals are described in commonly owned U.S. Pat. No. 7,555,335, which is hereby incorporated herein by reference.

Over the useful life of an implantable device, changes may occur in one or both of the patient and the implantable device. Certain changes may result in reduced capability of sensing cardiac activity. As an extreme example, consider the failure of an electrode element in an electrode array. Before the failure, the element may be used to determine the oriented cardiac sensing vector, but after the failure, the cardiac signal is lost. In this case, methods in accordance with the present invention may determine that the vector associated with the failed electrode is no longer the best vector to determine cardiac activity, and a next-best vector may be determined. The results of the separation/update process may be for the implantable device to update its cardiac sense vector to the newly established oriented vector.

Figure 3:
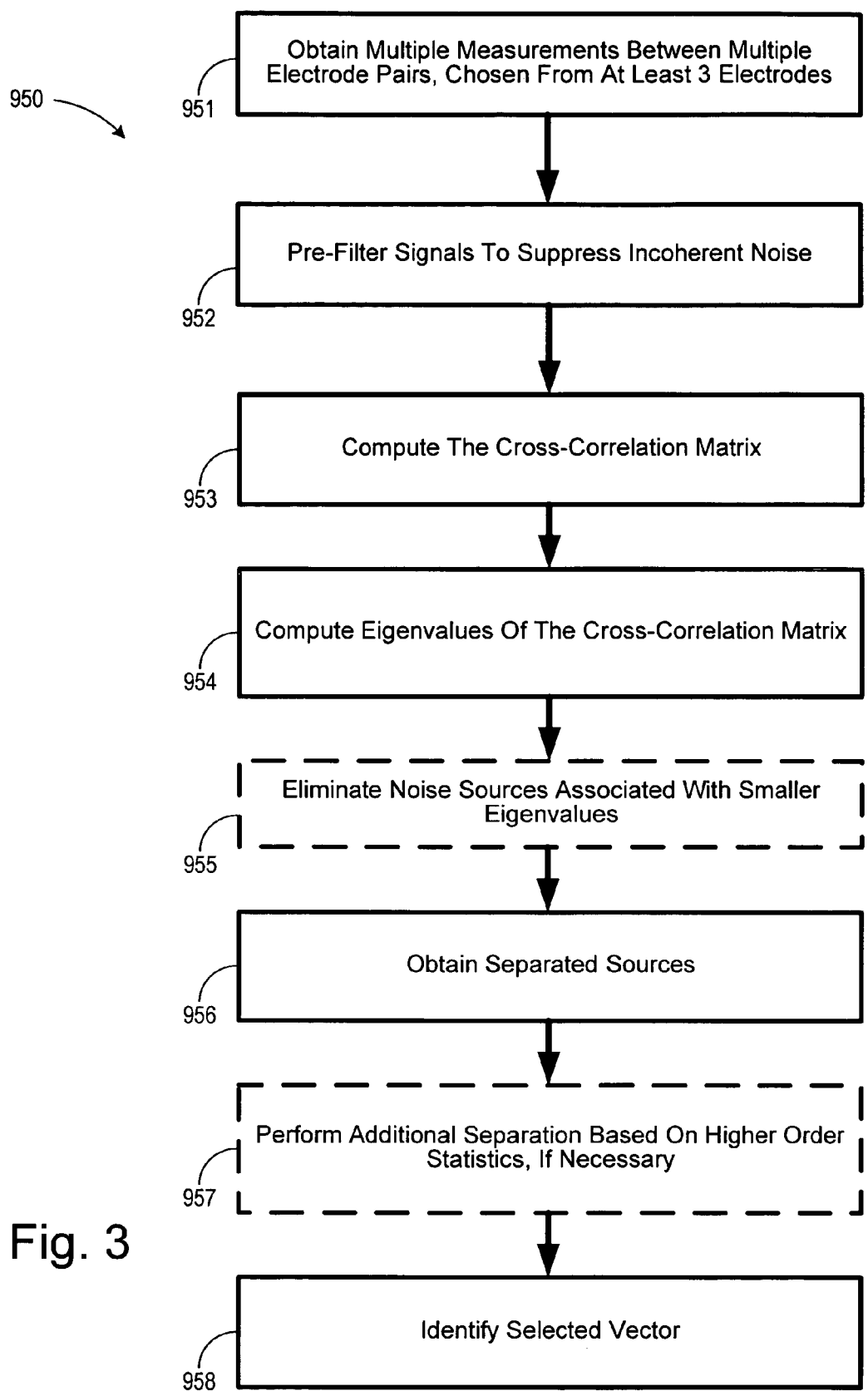
FIG. 3 is a block diagram of a vector selection process in accordance with the present invention.

FIG. 3 is block diagram of a vector selection process 950 useful for selecting and/or updating cardiac sense vectors in accordance with the present invention. The vector selection process 950 starts at block 951, where multiple concurrent measurements are obtained between multiple respective electrode pairs, chosen from at least three electrodes. Block 952 provides for pre-filtering the collected signals with, for example, a linear-phase filter to suppress broadly incoherent noise, and to generally maximize the signal-to-noise ratio.

Block 953 indicates the computation of the cross-correlation matrix, which may be averaged over a relatively short time interval, such as about 1 second. This block enhances the components that are mutually correlated. Block 954 is then provided for computation of the eigenvalues of the cross-correlation matrix. The smaller eigenvalues, normally associated with noise, may then be used at block 955 to eliminate noise, by removing the noise components of the composite signals associated with those eigenvalues.

At block 956, signals may be separated from the composite signals using the eigenvalues. Separated sources may be obtained by taking linear combinations of the recorded signals, as specified in the eigenvectors corresponding to the larger eigenvalues. Optionally, block 957 provides for performing additional separation based on higher order statistics, if the cardiac signal is not found among the signals separated at block 956.

At block 958, the oriented cardiac signal may be identified based on the selection criteria, along with its associated vector, among the separated signals. Typically, the signal is found among the signals associated with the largest eigenvalues. The vector associated with the oriented cardiac signal may then be selected as the vector to use in accordance with the present invention, that provides a cardiac signal that is indifferent to device orientation.

Signal separation methodologies and electrode and vector selection methodologies useful for orientationally insensitive cardiac devices are further described in commonly owned U.S. Pat. No. 7,706,866, which is hereby incorporated herein by reference.

Figure 4:
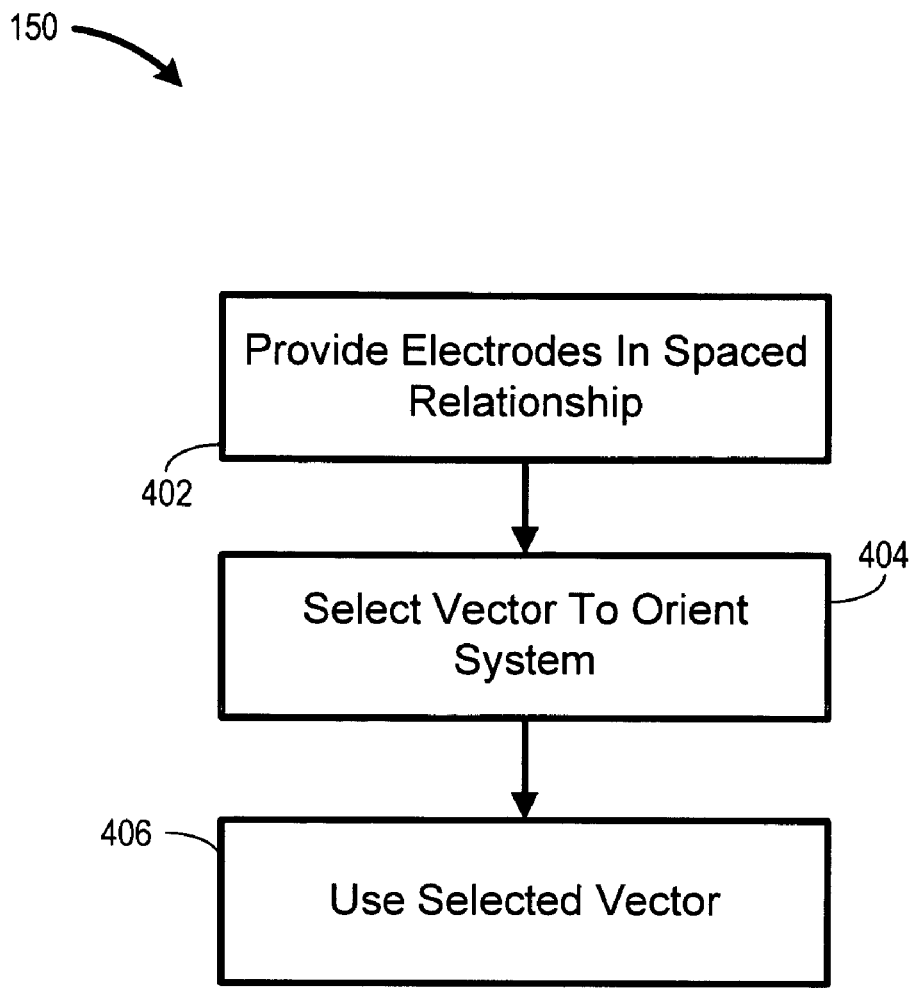
FIG. 4 is a block diagram of a cardiac sensing methodology incorporating signal separation for automatic adaptation to position and orientation in accordance with an embodiment of the present invention.

FIG. 4 is a block diagram of a cardiac sensing method 150 incorporating signal separation for automatic adaptation to position and orientation in accordance with an embodiment of the present invention. An implantable housing is provided 402, and supports multiple electrodes arranged in a spaced relationship in or on the housing. The housing and the electrodes may be configured for subcutaneous, non-intrathoracic placement in a patient. The electrodes may be selectively combinable to define sense vectors using a source separation methodology, as described previously. A sense vector is selected 404, which is useful for sensing cardiac activity. The selected sense vector is used 406 to facilitate sensing of cardiac activity irrespective of positional orientation of the housing within the patient.

Figure 5:
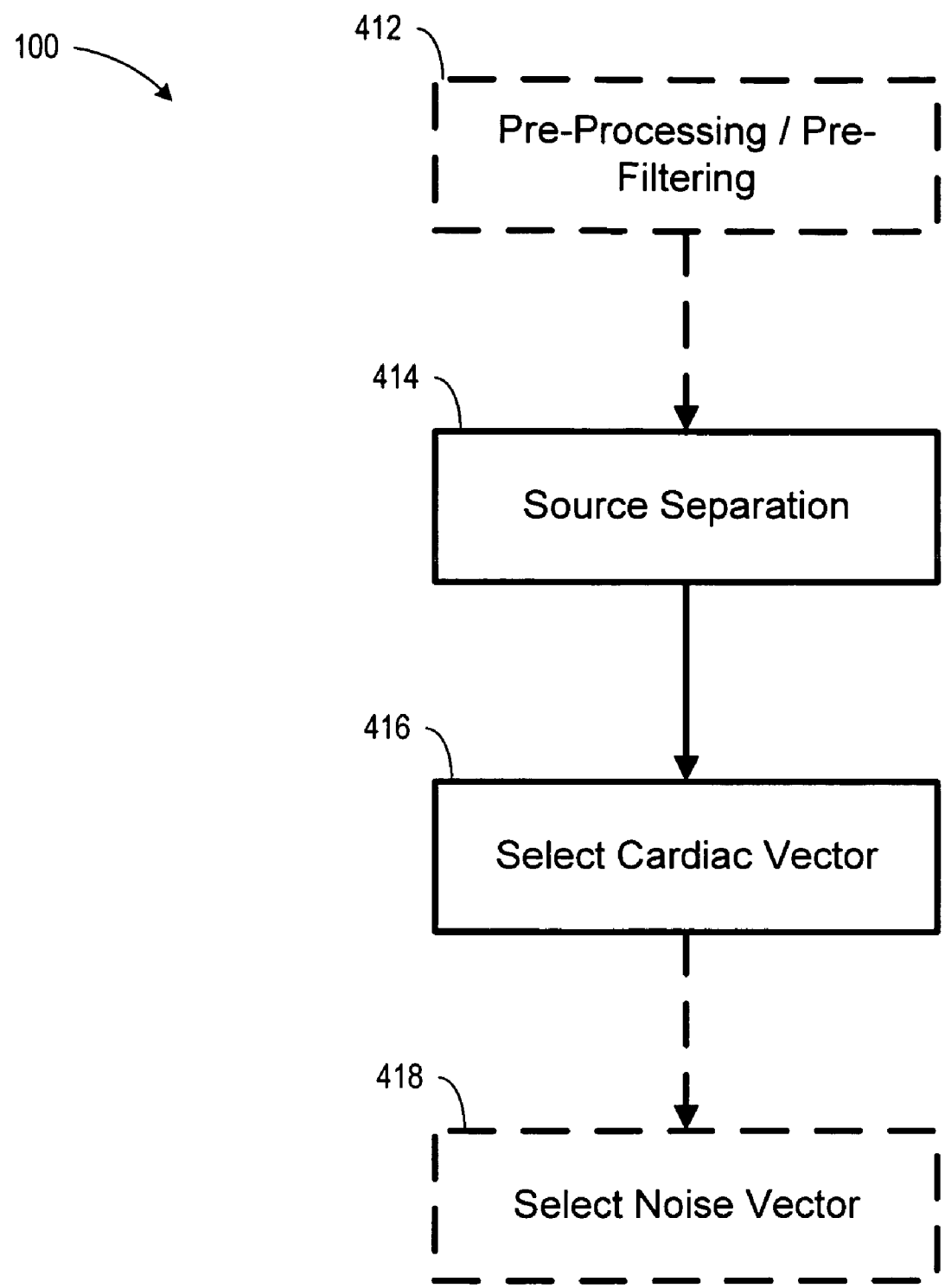
FIG. 5 is a block diagram of an implant orientation adaptation process in accordance with the present invention.

FIG. 5 is a block diagram of an implant orientation adaptation process 100 in accordance with embodiments of the present invention. An implantable device, such as is illustrated in FIGS. 2A through 2H, is implanted in a patient, and provides multiple combinations of vectors. An internal and/or external controller acquires composite signals from multiple electrodes. The composite signals may be pre-processed and/or pre-filtered 412 before performing a source separation 414. The source separation provides a number of separated source signals. The separated signals are analyzed by the controller and/or a clinician, and a cardiac vector 416 is chosen, which corresponds to a selected electrode combination that the implanted device may use for cardiac signal sensing. The separated signals may be further analyzed by the controller and/or a clinician, and a cardiac vector 418 may be chosen, which corresponds to a selected electrode combination that the implanted device may use for noise sensing and/or skeletal muscle sensing. The process 100 may be used to update the selected vector(s) as desired.

Updating the vector to regularly search for the oriented cardiac sense vector may be performed periodically or as otherwise desired. For example, an ITCS device may regularly perform an update of the sense vector used for cardiac discrimination, to keep performance of the ITCS improved and/or optimized. Updating may be useful, for example, when pathology, therapy, posture, or other system or patient change suggests a change in vector to separate the cardiac signal may be useful.

For example, in an APM environment such as will be described below, an ITCS in accordance with the present invention may have a controller and communications circuitry that transmits its cardiac composite signals to a bedside signal processor when the patient is asleep. The signal processor may perform a blind source separation and analysis of the composite signals during the patient's sleep cycle. The signal processor may then determine the appropriate vector or vectors for the ITCS, and reprogram the ITCS before the patient awakes. The ITCS may then operate with the latest programming until the next update.

Certain configurations illustrated herein are generally described as capable of implementing various functions traditionally performed by an implantable cardioverter/defibrillator (ICD), and may operate in numerous cardioversion/defibrillation modes as are known in the art. Examples of ICD circuitry, structures and functionality, aspects of which may be incorporated in an ITCS device of a type that may benefit from electrode orientation and vector updating methods and implementations are disclosed in commonly owned U.S. Pat. Nos. 5,133,353; 5,179,945; 5,314,459; 5,318,597; 5,620,466; and 5,662,688, which are hereby incorporated herein by reference.

In particular configurations, systems and methods may perform functions traditionally performed by pacemakers, such as providing various pacing therapies as are known in the art, in addition to cardioversion/defibrillation therapies. Examples of pacemaker circuitry, structures and functionality, aspects of which may be incorporated in an ITCS device of a type that may benefit from electrode orientation and vector updating methods and implementations are disclosed in commonly owned U.S. Pat. Nos. 4,562,841; 5,284,136; 5,376,106; 5,036,849; 5,540,727; 5,836,987; 6,044,298; and 6,055,454, which are hereby incorporated herein by reference. It is understood that ITCS device configurations may provide for non-physiologic pacing support in addition to, or to the exclusion of, bradycardia and/or anti-tachycardia pacing therapies.

An ITCS device in accordance with the present invention may implement diagnostic and/or monitoring functions as well as provide cardiac stimulation therapy. Examples of cardiac monitoring circuitry, structures and functionality, aspects of which may be incorporated in an ITCS device of a type that may benefit from electrode orientation and vector updating methods and implementations are disclosed in commonly owned U.S. Pat. Nos. 5,313,953; 5,388,578; and 5,411,031, which are hereby incorporated herein by reference.

Various embodiments described herein may be used in connection with congestive heart failure (CHF) monitoring, diagnosis, and/or therapy. An ITCS device of the present invention may incorporate CHF features involving dual-chamber or bi-ventricular pacing/therapy, cardiac resynchronization therapy, cardiac function optimization, or other CHF related methodologies. For example, and ITCS device of the present invention may incorporate features of one or more of the following references: commonly owned U.S. Pat. Nos. 6,411,848; 6,285,907; 4,928,688; 6,459,929; 5,334,222; 6,026,320; 6,371,922; 6,597,951; 6,424,865; 6,542,775; and 7,260,432, each of which is hereby incorporated herein by reference.

An ITCS device may be used to implement various diagnostic functions, which may involve performing rate-based, pattern and rate-based, and/or morphological tachyarrhythmia discrimination analyses. Subcutaneous, cutaneous, and/or external sensors may be employed to acquire physiologic and non-physiologic information for purposes of enhancing tachyarrhythmia detection and termination. It is understood that configurations, features, and combination of features described in the present disclosure may be implemented in a wide range of implantable medical devices, and that such embodiments and features are not limited to the particular devices described herein.

For purposes of clarity and understanding, further aspects of the present invention are herein described in reference to an implantable ITCS device. The primary housing (e.g., the active or non-active can) of the ITCS device, for example, may be configured for positioning outside of the rib cage at an intercostal or subcostal location, within the abdomen, or in the upper chest region (e.g., subclavian location, such as above the third rib). In one implementation, one or more electrodes may be located on the primary housing and/or at other locations about, but not in direct contact With the heart, great vessel or coronary vasculature.

In another implementation, one or more leads incorporating electrodes may be located in direct contact with the heart, great vessel or coronary vasculature, such as via one or more leads implanted by use of conventional transvenous delivery approaches. In a further implementation, for example, one or more electrode subsystems or electrode arrays may be used to sense cardiac activity and deliver cardiac stimulation energy in an ITCS device configuration employing an active can or a configuration employing a non-active can. Electrodes may be situated at anterior and/or posterior locations relative to the heart. Examples of noise canceling electrodes and electrode arrays are described in commonly owned U.S. Pat. No. 7,499,750, which is hereby incorporated herein by reference.

Certain configurations illustrated herein are generally described as capable of implementing various functions traditionally performed by an implantable cardioverter/defibrillator (ICD), and may operate in numerous cardioversion/defibrillation modes as are known in the art. Examples of ICD circuitry, structures and functionality, aspects of which may be incorporated in an ITCS device of a type that may benefit from electrode orientation and vector updating methods and devices are disclosed in commonly owned U.S. Pat. Nos. 5,133,353; 5,179,945; 5,314,459; 5,318,597; 5,620,466; and 5,662,688, which are hereby incorporated herein by reference.

In particular configurations, systems and methods may perform functions traditionally performed by pacemakers, such as providing various pacing therapies as are known in the art, in addition to cardioversion/defibrillation therapies. Examples of pacemaker circuitry, structures and functionality, aspects of which may be incorporated in an ITCS device of a type that may benefit from electrode orientation and vector updating methods and devices are disclosed in commonly owned U.S. Pat. Nos. 4,562,841; 5,284,136; 5,376,106; 5,036,849; 5,540,727; 5,836,987; 6,044,298; and 6,055,454, which are hereby incorporated herein by reference. It is understood that ITCS device configurations may provide for non-physiologic pacing support in addition to, or to the exclusion of, bradycardia and/or anti-tachycardia pacing therapies.

An ITCS device in accordance with the present invention may implement diagnostic and/or monitoring functions as well as provide cardiac stimulation therapy. Examples of cardiac monitoring circuitry, structures and functionality, aspects of which may be incorporated in an ITCS device of a type that may benefit from electrode orientation and vector updating methods and devices are disclosed in commonly owned U.S. Pat. Nos. 5,313,953; 5,388,578; and 5,411,031, which are hereby incorporated herein by reference.

An ITCS device may be used to implement various diagnostic functions, which may involve performing rate-based, pattern and rate-based, and/or morphological tachyarrhythmia discrimination analyses. Subcutaneous, cutaneous, and/or external sensors may be employed to acquire physiologic and non-physiologic information for purposes of enhancing tachyarrhythmia detection and termination. It is understood that configurations, features, and combination of features described in the present disclosure may be implemented in a wide range of implantable medical devices, and that such embodiments and features are not limited to the particular devices described herein.

Figure 6A:
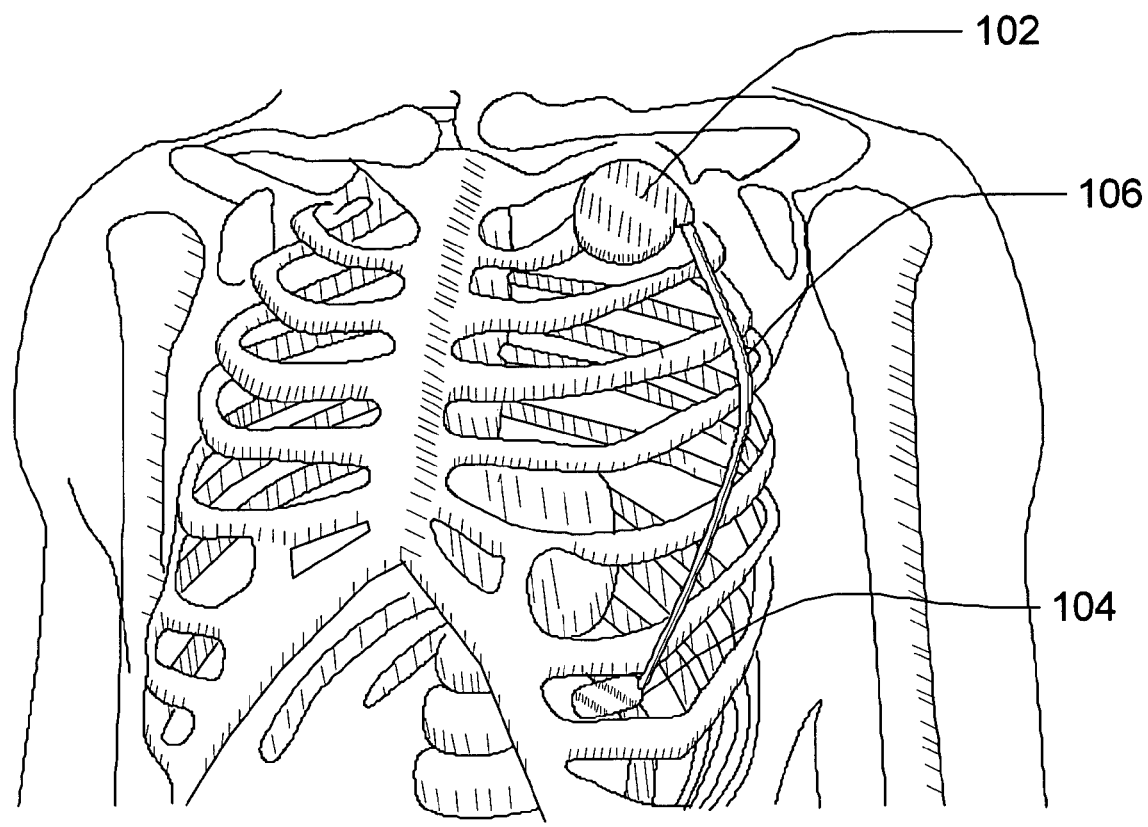
FIGS. 6A and 6B are views of a cardiac sensing and/or stimulation device as implanted in a patient in accordance with an embodiment of the present invention.
Figure 6B:
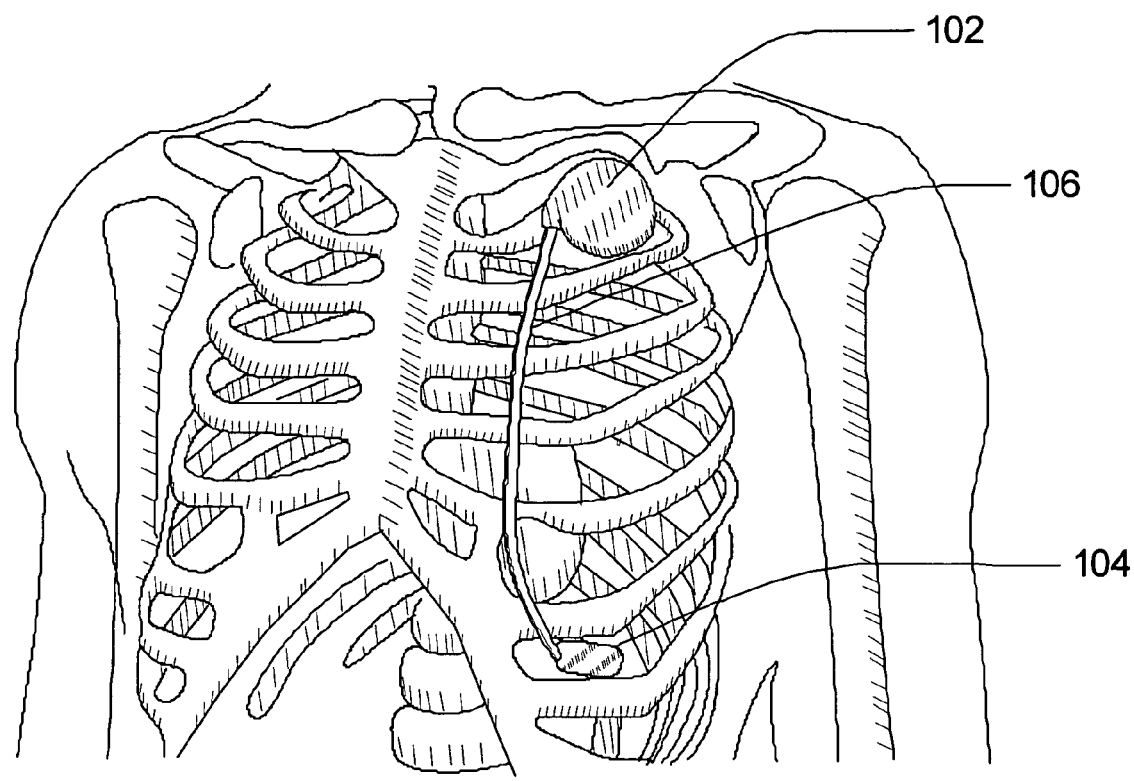

Referring now to FIGS. 6A and 6B of the drawings, there is shown a configuration of a cardiac sensing and/or stimulation (ITCS) device having components implanted in the chest region of a patient at different locations. In the particular configuration shown in FIGS. 6A and 6B, the ITCS device includes a housing 102 within which various cardiac sensing, detection, processing, and energy delivery circuitry may be housed. It is understood that the components and functionality depicted in the figures and described herein may be implemented in hardware, software, or a combination of hardware and software. It is further understood that the components and functionality depicted as separate or discrete blocks/elements in the figures may be implemented in combination with other components and functionality, and that the depiction of such components and functionality in individual or integral form is for purposes of clarity of explanation, and not of limitation.

Communications circuitry is disposed within the housing 102 for facilitating communication between the ITCS device and an external communication device, such as a portable or bed-side communication station, patient-carried/worn communication station, or external programmer, for example. The communications circuitry may also facilitate unidirectional or bidirectional communication with one or more external, cutaneous, or physiologic or non-physiologic sensors. The housing 102 is typically configured to include one or more electrodes (e.g., can electrode and/or indifferent electrode). Although the housing 102 is typically configured as an active can, it is appreciated that a non-active can configuration may be implemented, in which case at least two electrodes spaced apart from the housing 102 are employed.

In the configuration shown in FIGS. 6A and 6B, an electrode 104 may be positioned under the skin in the chest region and situated distal from the housing 102. If applicable, housing electrode(s) may be positioned about the heart at various locations and orientations, such as at various anterior and/or posterior locations relative to the heart. The electrode 104 is coupled to circuitry within the housing 102 via a lead assembly 106. One or more conductors (e.g., coils or cables) are provided within the lead assembly 106 and electrically couple the electrode 104 with circuitry in the housing 102. One or more sense, sense/pace or defibrillation electrodes may be situated on the elongated structure of the electrode support, the housing 102, and/or the distal electrode assembly (shown as electrode 104 in the configuration shown in FIGS. 6A and 6B).

In one configuration, the lead assembly 106 is generally flexible and has a construction similar to conventional implantable, medical electrical leads (e.g., defibrillation leads or combined defibrillation/pacing leads). In another configuration, the lead assembly 106 is constructed to be somewhat flexible, yet has an elastic, spring, or mechanical memory that retains a desired configuration after being shaped or manipulated by a clinician. For example, the lead assembly 106 may incorporate a gooseneck or braid system that may be distorted under manual force to take on a desired shape. In this manner, the lead assembly 106 may be shape-fit to accommodate the unique anatomical configuration of a given patient, and generally retains a customized shape after implantation. Shaping of the lead assembly 106 according to this configuration may occur prior to, and during, ITCS device implantation.

In accordance with a further configuration, the lead assembly 106 includes a rigid electrode support assembly, such as a rigid elongated structure that positionally stabilizes the electrode 104 with respect to the housing 102. In this configuration, the rigidity of the elongated structure maintains a desired spacing between the electrode 104 and the housing 102, and a desired orientation of the electrode 104/housing 102 relative to the patient's heart. The elongated structure may be formed from a structural plastic, composite or metallic material, and includes, or is covered by, a biocompatible material. Appropriate electrical isolation between the housing 102 and electrode 104 is provided in cases where the elongated structure is formed from an electrically conductive material, such as metal.

In one configuration, the rigid electrode support assembly and the housing 102 define a unitary structure (e.g., a single housing/unit). The electronic components and electrode conductors/connectors are disposed within or on the unitary ITCS device housing/electrode support assembly. At least two electrodes are supported on the unitary structure near opposing ends of the housing/electrode support assembly. The unitary structure may have an arcuate or angled shape, for example.

According to another configuration, the rigid electrode support assembly defines a physically separable unit relative to the housing 102. The rigid electrode support assembly includes mechanical and electrical couplings that facilitate mating engagement with corresponding mechanical and electrical couplings of the housing 102. For example, a header block arrangement may be configured to include both electrical and mechanical couplings that provide for mechanical and electrical connections between the rigid electrode support assembly and housing 102. The header block arrangement may be provided on the housing 102 or the rigid electrode support assembly. Alternatively, a mechanical/electrical coupler may be used to establish mechanical and electrical connections between the rigid electrode support assembly and housing 102. In such a configuration, a variety of different electrode support assemblies of varying shapes, sizes, and electrode configurations may be made available for physically and electrically connecting to a standard ITCS device housing 102.

It is noted that the electrodes and the lead assembly 106 may be configured to assume a variety of shapes. For example, the lead assembly 106 may have a wedge, chevron, flattened oval, or a ribbon shape, and the electrode 104 may include a number of spaced electrodes, such as an array or band of electrodes. Moreover, two or more electrodes 104 may be mounted to multiple electrode support assemblies 106 to achieve a desired spaced relationship amongst electrodes 104.

An ITCS device may incorporate circuitry, structures and functionality of the implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243, which are hereby incorporated herein by reference.

Figure 6C:
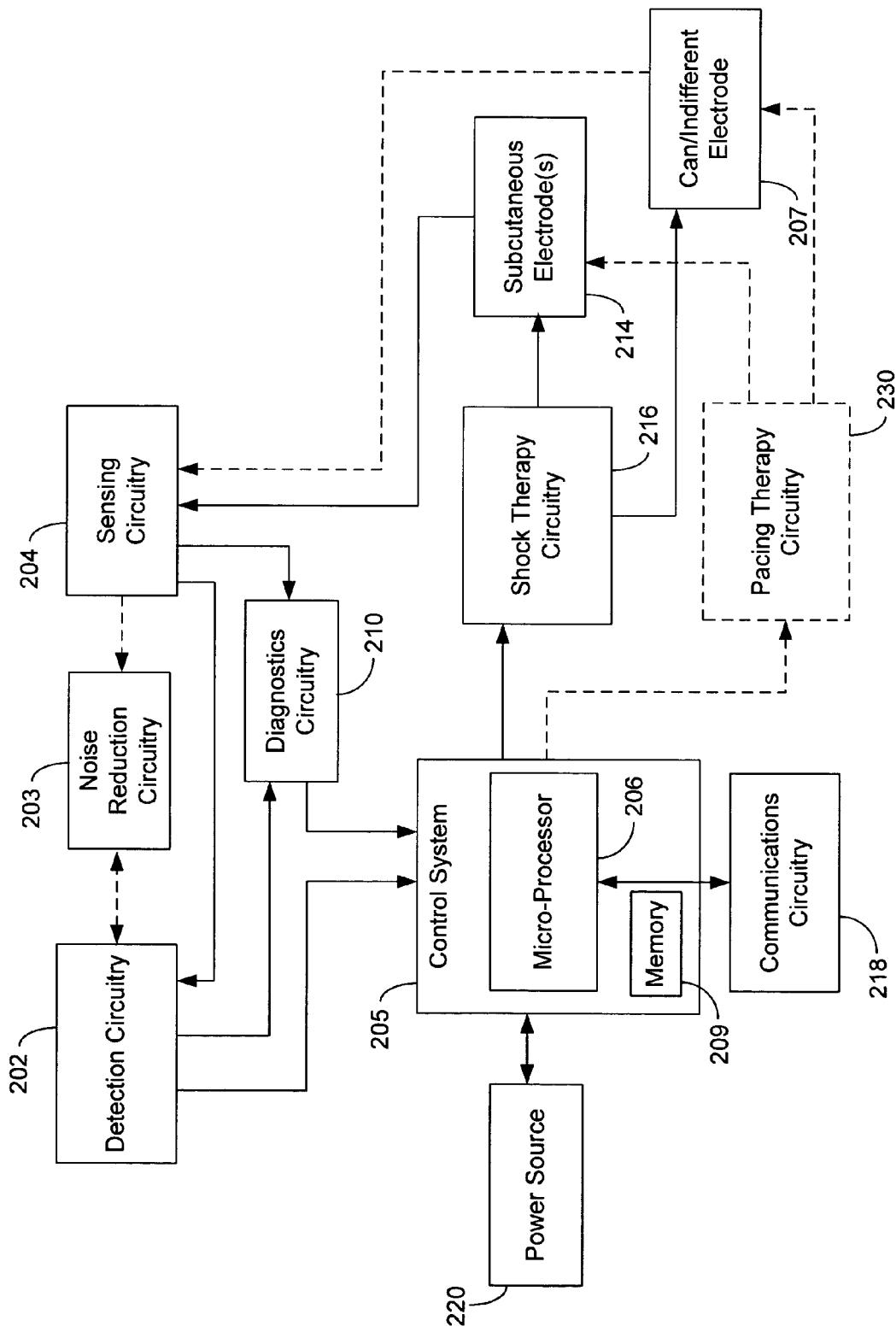
FIG. 6C is a block diagram illustrating various components of a cardiac sensing and/or stimulation device in accordance with an embodiment of the present invention.

FIG. 6C is a block diagram depicting various components of an ITCS device in accordance with one configuration. According to this configuration, the ITCS device incorporates a processor-based control system 205 which includes a micro-processor 206 coupled to appropriate memory 209 (volatile and/or non-volatile), it being understood that any logic-based control architecture may be used. The control system 205 is coupled to circuitry and components to sense, detect, and analyze electrical signals produced by the heart and deliver electrical stimulation energy to the heart under predetermined conditions to treat cardiac arrhythmias. In certain configurations, the control system 205 and associated components also provide pacing therapy to the heart. The electrical energy delivered by the ITCS device may be in the form of low energy pacing pulses or high-energy pulses for cardioversion or defibrillation.

Cardiac signals are sensed using the electrode(s) 214 and the can or indifferent electrode 207 provided on the ITCS device housing. Cardiac signals may also be sensed using only the electrodes 214, such as in a non-active can configuration. As such, unipolar, bipolar, or combined unipolar/bipolar electrode configurations as well as multi-element electrodes and combinations of noise canceling and standard electrodes may be employed. The sensed cardiac signals are received by sensing circuitry 204, which includes sense amplification circuitry and may also include filtering circuitry and an analog-to-digital (A/D) converter. The sensed cardiac signals processed by the sensing circuitry 204 may be received by noise reduction circuitry 203, which may further reduce noise before signals are sent to the detection circuitry 202.

Noise reduction circuitry 203 may also be incorporated after sensing circuitry 202 in cases where high power or computationally intensive noise reduction algorithms are required. The noise reduction circuitry 203, by way of amplifiers used to perform operations with the electrode signals, may also perform the function of the sensing circuitry 204. Combining the functions of sensing circuitry 204 and noise reduction circuitry 203 may be useful to minimize the necessary componentry and lower the power requirements of the system.

In the illustrative configuration shown in FIG. 6C, the detection circuitry 202 is coupled to, or otherwise incorporates, noise reduction circuitry 203. The noise reduction circuitry 203 operates to improve the SNR of sensed cardiac signals by removing noise content of the sensed cardiac signals introduced from various sources. Typical types of cardiac signal noise includes electrical noise and noise produced from skeletal muscles, for example. A number of methodologies for improving the SNR of sensed cardiac signals in the presence of skeletal muscular induced noise, including signal separation techniques incorporating combinations of electrodes and multi-element electrodes, are described hereinbelow.

Detection circuitry 202 typically includes a signal processor that coordinates analysis of the sensed cardiac signals and/or other sensor inputs to detect cardiac arrhythmias, such as, in particular, tachyarrhythmia. Rate based and/or morphological discrimination algorithms may be implemented by the signal processor of the detection circuitry 202 to detect and verify the presence and severity of an arrhythmic episode. Examples of arrhythmia detection and discrimination circuitry, structures, and techniques, aspects of which may be implemented by an ITCS device of a type that may benefit from electrode orientation and vector updating methods and devices are disclosed in commonly owned U.S. Pat. Nos. 5,301,677 and 6,438,410, which are hereby incorporated herein by reference. Arrhythmia detection methodologies particularly well suited for implementation in cardiac monitoring and/or stimulation systems are described hereinbelow.

The detection circuitry 202 communicates cardiac signal information to the control system 205. Memory circuitry 209 of the control system 205 contains parameters for operating in various sensing, defibrillation, and, if applicable, pacing modes, and stores data indicative of cardiac signals received by the detection circuitry 202. The memory circuitry 209 may also be configured to store historical ECG and therapy data, which may be used for various purposes and transmitted to an external receiving device as needed or desired.

In certain configurations, the ITCS device may include diagnostics circuitry 210. The diagnostics circuitry 210 typically receives input signals from the detection circuitry 202 and the sensing circuitry 204. The diagnostics circuitry 210 provides diagnostics data to the control system 205, it being understood that the control system 205 may incorporate all or part of the diagnostics circuitry 210 or its functionality. The control system 205 may store and use information provided by the diagnostics circuitry 210 for a variety of diagnostics purposes. This diagnostic information may be stored, for example, subsequent to a triggering event or at predetermined intervals, and may include system diagnostics, such as power source status, therapy delivery history, and/or patient diagnostics. The diagnostic information may take the form of electrical signals or other sensor data acquired immediately prior to therapy delivery.

According to a configuration that provides cardioversion and defibrillation therapies, the control system 205 processes cardiac signal data received from the detection circuitry 202 and initiates appropriate tachyarrhythmia therapies to terminate cardiac arrhythmic episodes and return the heart to normal sinus rhythm. The control system 205 is coupled to shock therapy circuitry 216. The shock therapy circuitry 216 is coupled to the electrode(s) 214 and the can or indifferent electrode 207 of the ITCS device housing. Upon command, the shock therapy circuitry 216 delivers cardioversion and defibrillation stimulation energy to the heart in accordance with a selected cardioversion or defibrillation therapy. In a less sophisticated configuration, the shock therapy circuitry 216 is controlled to deliver defibrillation therapies, in contrast to a configuration that provides for delivery of both cardioversion and defibrillation therapies. Examples of ICD high energy delivery circuitry, structures and functionality, aspects of which may be incorporated in an ITCS device of a type that may benefit from aspects of the present invention are disclosed in commonly owned U.S. Pat. Nos. 5,372,606; 5,411,525; 5,468,254; and 5,634,938, which are hereby incorporated herein by reference.

In accordance with another configuration, an ITCS device may incorporate a cardiac pacing capability in addition to cardioversion and/or defibrillation capabilities. As is shown in dotted lines in FIG. 6C, the ITCS device may include pacing therapy circuitry 230 which is coupled to the control system 205 and the and can/indifferent electrodes 214, 207. Upon command, the pacing therapy circuitry delivers pacing pulses to the heart in accordance with a selected pacing therapy. Control signals, developed in accordance with a pacing regimen by pacemaker circuitry within the control system 205, are initiated and transmitted to the pacing therapy circuitry 230 where pacing pulses are generated. A pacing regimen may be modified by the control system 205.

A number of cardiac pacing therapies may be useful in a cardiac monitoring and/or stimulation device. Such cardiac pacing therapies may be delivered via the pacing therapy circuitry 230 as shown in FIG. 6C. Alternatively, cardiac pacing therapies may be delivered via the shock therapy circuitry 216, which effectively obviates the need for separate pacemaker circuitry.

The ITCS device shown in FIG. 6C may be configured to receive signals from one or more physiologic and/or non-physiologic sensors. Depending on the type of sensor employed, signals generated by the sensors may be communicated to transducer circuitry coupled directly to the detection circuitry 202 or indirectly via the sensing circuitry 204. It is noted that certain sensors may transmit sense data to the control system 205 without processing by the detection circuitry 202.

Communications circuitry 218 is coupled to the microprocessor 206 of the control system 205. The communications circuitry 218 allows the ITCS device to communicate with one or more receiving devices or systems situated external to the ITCS device. By way of example, the ITCS device may communicate with a patient-worn, portable or bedside communication system via the communications circuitry 218. In one configuration, one or more physiologic or non-physiologic sensors (subcutaneous, cutaneous, or external of patient) may be equipped with a short-range wireless communication interface, such as an interface conforming to a known communications standard, such as Bluetooth or IEEE 802 standards. Data acquired by such sensors may be communicated to the ITCS device via the communications circuitry 218. It is noted that physiologic or non-physiologic sensors equipped with wireless transmitters or transceivers may communicate with a receiving system external of the patient.

The communications circuitry 218 may allow the ITCS device to communicate with an external programmer. In one configuration, the communications circuitry 218 and the programmer unit (not shown) use a wire loop antenna and a radio frequency telemetric link, as is known in the art, to receive and transmit signals and data between the programmer unit and communications circuitry 218. In this manner, programming commands and data are transferred between the ITCS device and the programmer unit during and after implant. Using a programmer, a physician is able to set or modify various parameters used by the ITCS device. For example, a physician may set or modify parameters affecting sensing, detection, pacing, and defibrillation functions of the ITCS device, including pacing and cardioversion/defibrillation therapy modes.

Typically, the ITCS device is encased and hermetically sealed in a housing suitable for implanting in a human body as is known in the art. Power to the ITCS device is supplied by an electrochemical power source 220 housed within the ITCS device. In one configuration, the power source 220 includes a rechargeable battery. According to this configuration, charging circuitry is coupled to the power source 220 to facilitate repeated non-invasive charging of the power source 220. The communications circuitry 218, or separate receiver circuitry, is configured to receive RF energy transmitted by an external RF energy transmitter. The ITCS device may, in addition to a rechargeable power source, include a non-rechargeable battery. It is understood that a rechargeable power source need not be used, in which case a long-life non-rechargeable battery is employed.

Figure 6D:
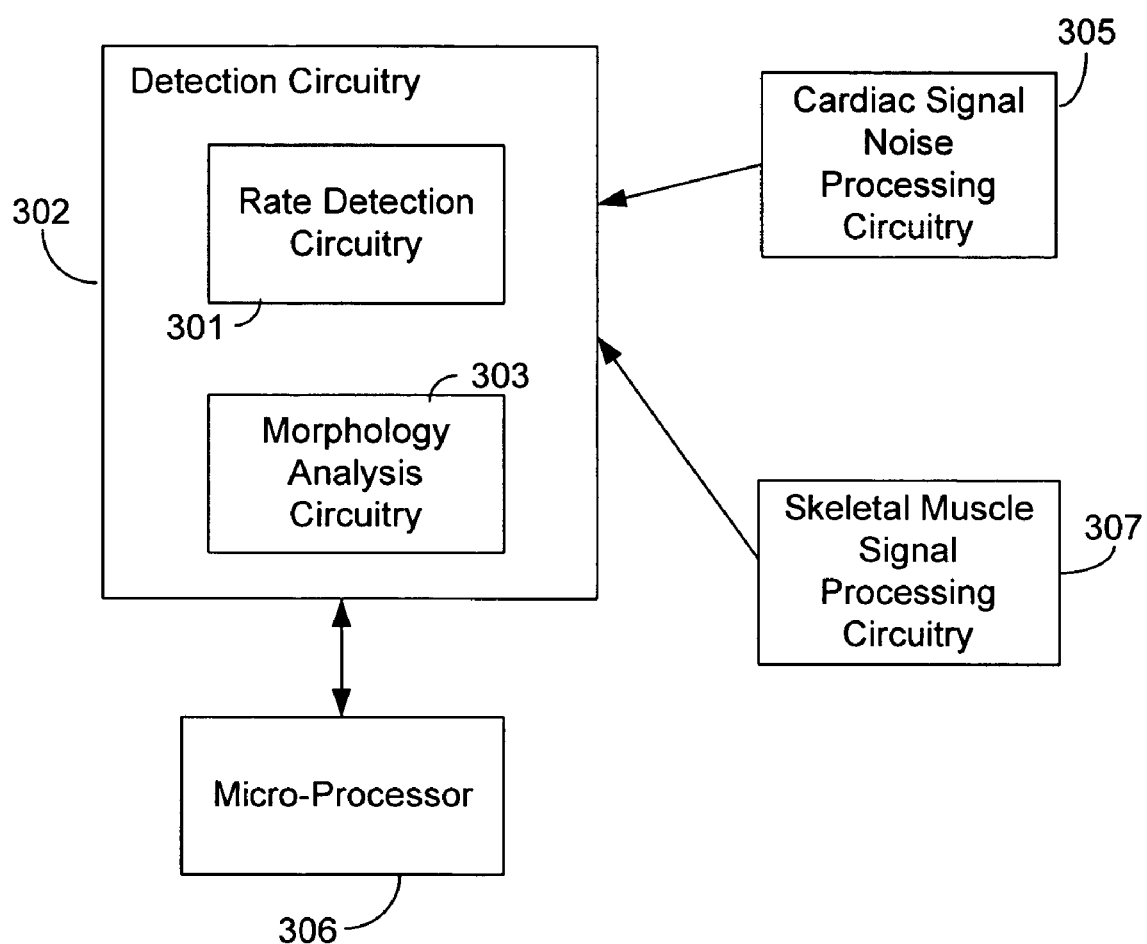
FIG. 6D is a block diagram illustrating various processing and detection components of a cardiac sensing and/or stimulation device in accordance with an embodiment of the present invention.

FIG. 6D illustrates a configuration of detection circuitry 302 of an ITCS device, which includes one or both of rate detection circuitry 301 and morphological analysis circuitry 303. Detection and verification of arrhythmias may be accomplished using rate-based discrimination algorithms as known in the art implemented by the rate detection circuitry 301. Arrhythmic episodes may also be detected and verified by morphology-based analysis of sensed cardiac signals as is known in the art. Tiered or parallel arrhythmia discrimination algorithms may also be implemented using both rate-based and morphologic-based approaches. Further, a rate and pattern-based arrhythmia detection and discrimination approach may be employed to detect and/or verify arrhythmic episodes, such as the approach disclosed in U.S. Pat. Nos. 6,487,443; 6,259,947; 6,141,581; 5,855,593; and 5,545,186, which are hereby incorporated herein by reference.

The detection circuitry 302, which is coupled to a microprocessor 306, may be configured to incorporate, or communicate with, specialized circuitry for processing sensed cardiac signals in manners particularly useful in a cardiac sensing and/or stimulation device. As is shown by way of example in FIG. 6D, the detection circuitry 302 may receive information from multiple physiologic and non-physiologic sensors.

The detection circuitry 302 may also receive information from one or more sensors that monitor skeletal muscle activity. In addition to cardiac activity signals, electrodes readily detect skeletal muscle signals. Such skeletal muscle signals may be used to determine the activity level of the patient. In the context of cardiac signal detection, such skeletal muscle signals are considered artifacts of the cardiac activity signal, which may be viewed as noise. Processing circuitry 307 receives signals from one or more skeletal muscle sensors, and transmits processed skeletal muscle signal data to the detection circuitry 302. This data may be used to discriminate normal cardiac sinus rhythm with skeletal muscle noise from cardiac arrhythmias.

As was previously discussed, the detection circuitry 302 is coupled to, or otherwise incorporates, noise-processing circuitry 305. The noise processing circuitry 305 processes sensed cardiac signals to improve the SNR of sensed cardiac signals by reducing noise content of the sensed cardiac signals.

The components, functionality, and structural configurations depicted in FIGS. 6A-6D are intended to provide an understanding of various features and combination of features that may be incorporated in an ITCS device. It is understood that a wide variety of ITCS and other implantable cardiac monitoring and/or stimulation device configurations are contemplated, ranging from relatively sophisticated to relatively simple designs. As such, particular ITCS or cardiac monitoring and/or stimulation device configurations may include particular features as described herein, while other such device configurations may exclude particular features described herein.

In accordance with embodiments of the invention, an ITCS device may be implemented to include an electrode system that provides for one or both of cardiac sensing and arrhythmia therapy delivery. According to one approach, an ITCS device may be implemented as a chronically implantable system that performs monitoring, diagnostic and/or therapeutic functions. The ITCS device may automatically detect and treat cardiac arrhythmias. In one configuration, the ITCS device includes a pulse generator and one or more electrodes that are implanted subcutaneously in the chest region of the body, such as in the anterior thoracic region of the body. The ITCS device may be used to provide atrial and ventricular therapy for bradycardia and tachycardia arrhythmias. Tachyarrhythmia therapy may include cardioversion, defibrillation and anti-tachycardia pacing (ATP), for example, to treat atrial or ventricular tachycardia or fibrillation. Bradycardia therapy may include temporary post-shock pacing for bradycardia or asystole. Methods and systems for implementing post-shock pacing for bradycardia or asystole are described in commonly owned U.S. Pat. No. 7,392,081, which is incorporated herein by reference in its entirety.

In one configuration, an ITCS device according to one approach may utilize conventional pulse generator and electrode implant techniques. The pulse generator device and electrodes may be chronically implanted subcutaneously. Such an ITCS may be used to automatically detect and treat arrhythmias similarly to conventional implantable systems. In another configuration, the ITCS device may include a unitary structure (e.g., a single housing/unit). The electronic components and electrode conductors/connectors are disposed within or on the unitary ITCS device housing/electrode support assembly.

The ITCS device contains the electronics and may be similar to a conventional implantable defibrillator. High voltage shock therapy may be delivered between two or more electrodes, one of which may be the pulse generator housing (e.g., can), placed subcutaneously in the thoracic region of the body.

Additionally or alternatively, the ITCS device may also provide lower energy electrical stimulation for bradycardia therapy. The ITCS device may provide brady pacing similarly to a conventional pacemaker. The ITCS device may provide temporary post-shock pacing for bradycardia or asystole. Sensing and/or pacing may be accomplished using sense/pace electrodes positioned on an electrode subsystem also incorporating shock electrodes, or by separate electrodes implanted subcutaneously.

Figure 6E:
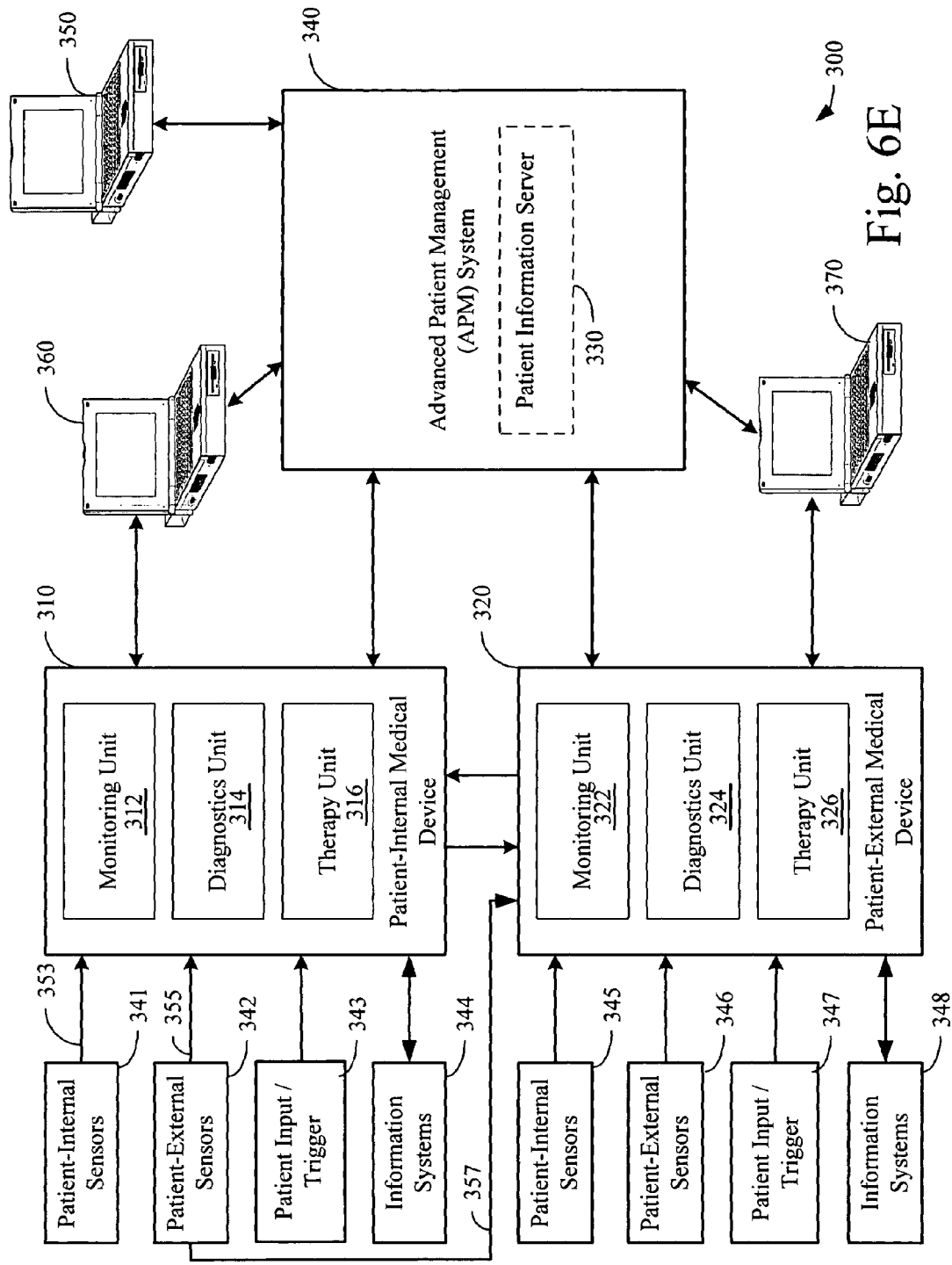
FIG. 6E is a block diagram of a medical system that may be used to implement system updating, coordinated patient monitoring, diagnosis, and/or therapy in accordance with embodiments of the present invention.

Referring now to FIG. 6E, the ITCS device may be used within the structure of an advanced patient management (APM) medical system 300. Advanced patient management systems may allow physicians to remotely and automatically monitor cardiac and respiratory functions, as well as other patient conditions. In one example, implantable cardiac rhythm management systems, such as cardiac pacemakers, defibrillators, and resynchronization devices, may be equipped with various telecommunications and information technologies that enable real-time data collection, diagnosis, and treatment of the patient. Various embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

As is illustrated in FIG. 6E, the medical system 300 may be used to implement coordinated patient measuring and/or monitoring, diagnosis, and/or therapy in accordance with embodiments of the invention. The medical system 300 may include, for example, one or more patient-internal medical devices 310, such as an ITCS device, and one or more patient-external medical devices 320, such as a monitor or signal display device. Each of the patient-internal 310 and patient-external 320 medical devices may include one or more of a patient monitoring unit 312, 322, a diagnostics unit 314, 324, and/or a therapy unit 316, 326.

The patient-external medical device 320 performs monitoring, and/or diagnosis and/or therapy functions external to the patient (i.e., not invasively implanted within the patient's body). The patient-external medical device 320 may be positioned on the patient, near the patient, or in any location external to the patient.

The patient-internal and patient-external medical devices 310, 320 may be coupled to one or more sensors 341, 342, 345, 346, patient input/trigger devices 343, 347 and/or other information acquisition devices 344, 348. The sensors 341, 342, 345, 346, patient input/trigger devices 343, 347, and/or other information acquisition devices 344, 348 may be employed to detect conditions relevant to the monitoring, diagnostic, and/or therapeutic functions of the patient-internal and patient-external medical devices 310, 320.

The medical devices 310, 320 may each be coupled to one or more patient-internal sensors 341, 345 that are fully or partially implantable within the patient. The medical devices 310, 320 may also be coupled to patient-external sensors positioned on, near, or in a remote location with respect to the patient. The patient-internal and patient-external sensors are used to sense conditions, such as physiological or environmental conditions, that affect the patient.

The patient-internal sensors 341 may be coupled to the patient-internal medical device 310 through one or more internal leads 353. Still referring to FIG. 6E, one or more patient-internal sensors 341 may be equipped with transceiver circuitry to support wireless communications between the one or more patient-internal sensors 341 and the patient-internal medical device 310 and/or the patient-external medical device 320.

The patient-external sensors 342 may be coupled to the patient-internal medical device 310 and/or the patient-external medical device 320 through one or more internal leads 355 or through wireless connections. Patient-external sensors 342 may communicate with the patient-internal medical device 310 wirelessly. Patient-external sensors 346 may be coupled to the patient-external medical device 320 through one or more internal leads 357 or through a wireless link.

Referring still to FIG. 6E, the medical devices 310, 320 may be connected to one or more information acquisition devices 344, 348, such as a database that stores information useful in connection with the monitoring, diagnostic, or therapy functions of the medical devices 310, 320. For example, one or more of the medical devices 310, 320 may be coupled through a network to a patient information server 330.

In one embodiment, the patient-internal medical device 310 and the patient-external medical device 320 may communicate through a wireless link between the medical devices 310, 320. For example, the patient-internal and patient-external devices 310, 320 may be coupled through a short-range radio link, such as Bluetooth, IEEE 802.11, and/or a proprietary wireless protocol. The communications link may facilitate uni-directional or bi-directional communication between the patient-internal 310 and patient-external 320 medical devices. Data and/or control signals may be transmitted between the patient-internal 310 and patient-external 320 medical devices to coordinate the functions of the medical devices 310, 320.

In another embodiment, patient data may be downloaded from one or more of the medical devices periodically or on command, and stored at the patient information server 330. The physician and/or the patient may communicate with the medical devices and the patient information server 330, for example, to acquire patient data or to initiate, terminate or modify recording and/or therapy.

The data stored on the patient information server 330 may be accessible by the patient and the patient's physician through one or more terminals 350, e.g., remote computers located in the patient's home or the physician's office. The patient information server 330 may be used to communicate to one or more of the patient-internal and patient-external medical devices 310, 320 to provide remote control of the monitoring, diagnosis, and/or therapy functions of the medical devices 310, 320.

In one embodiment, the patient's physician may access patient data transmitted from the medical devices 310, 320 to the patient information server 330. After evaluation of the patient data, the patient's physician may communicate with one or more of the patient-internal or patient-external devices 310, 320 through an APM system 340 to initiate, terminate, or modify the monitoring, diagnostic, and/or therapy functions of the patient-internal and/or patient-external medical systems 310, 320.

In another embodiment, the patient-internal and patient-external medical devices 310, 320 may not communicate directly, but may communicate indirectly through the APM system 340. In this embodiment, the APM system 340 may operate as an intermediary between two or more of the medical devices 310, 320. For example, data and/or control information may be transferred from one of the medical devices 310, 320 to the APM system 340. The APM system 340 may transfer the data and/or control information to another of the medical devices 310, 320.

In one embodiment, the APM system 340 may communicate directly with the patient-internal and/or patient-external medical devices 310, 320. In another embodiment, the APM system 340 may communicate with the patient-internal and/or patient-external medical devices 310, 320 through medical device programmers 360, 370 respectively associated with each medical device 310, 320.

An ITCS device may operate in a batch mode or adaptively, allowing for on-line or off-line implementation. To save power, the system may include the option for a hierarchical decision-making routine that uses algorithms known in the art for identifying presence of arrhythmias or noise in the collected signal and turning on the cardiac signal extraction routine.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. An implantable cardiac device, comprising:
   a housing having a first face opposing a second face, and an edge extending from a perimeter of the first face to a perimeter of the second face;
   a pulse generator comprising a controller provided in the housing; and
   a plurality of electrodes coupled to the pulse generator and arranged in a spaced relationship on the housing, the plurality of electrodes comprising at least three electrodes positioned on the edge of the housing and wrapping over a portion of the first and second faces of the housing;
   the controller configured to measure a plurality of signals using a plurality of electrode combinations and to automatically select a particular electrode combination of the plurality of electrode combinations that provides for improved cardiac signal sensing relative to other ones of the plurality of electrode combinations based on the measured signals, and controller selection of the particular electrode combination provides for sensing a cardiac signal having an amplitude or signal-to-noise ratio that exceeds a predetermined threshold.

2. The device of claim 1, wherein the arrangement of the plurality of electrodes facilitates controller selection of the particular electrode combination that provides for sensing of cardiac activity irrespective of changes in positional orientation of the housing within the patient.

3. The device of claim 1, wherein the arrangement of the plurality of electrodes facilitates controller selection of the particular electrode combination that provides for sensing of cardiac activity irrespective of rotation of the housing within the patient.

4. The device of claim 1, wherein the arrangement of the plurality of electrodes facilitates controller selection of the particular electrode combination that provides for sensing of cardiac activity irrespective of which of the first and second faces of the housing is orientated toward the patient's skin.

5. The device of claim 1, wherein the arrangement of the plurality of electrodes facilitates controller selection of the particular electrode combination that provides for sensing of cardiac activity irrespective of both of rotation of the housing within the patient and which of the first and second faces of the housing is orientated toward the patient's skin.

6. The device of claim 1, wherein the arrangement of the plurality of electrodes facilitates controller selection of a first electrode combination that preferentially provides for sensing of cardiac activity and a second electrode combination that preferentially provides for sensing of skeletal muscle activity.

7. The device of claim 1, wherein the pulse generator is configured to deliver defibrillation or cardioversion energy.

8. The device of claim 1, wherein the controller is configured to determine cardiac rhythm states using selected electrode combinations of the plurality of electrodes.

9. An implantable cardiac device, comprising:
- a housing having a first face opposing a second face, and an edge extending from a perimeter of the first face to a perimeter of the second face;
- a pulse generator comprising a controller provided in the housing; and
- a plurality of electrodes coupled to the pulse generator and arranged in a spaced relationship on the housing;
- the controller configured to measure a plurality of signals using a plurality of electrode combinations and to automatically select a particular electrode combination of the plurality of electrode combinations that provides for improved cardiac signal sensing relative to other ones of the plurality of electrode combinations based on the measured signals, the plurality of electrodes comprising at least three electrodes positioned on the edge of the housing and wrapping over a portion of the first and second faces of the housing.

10. The device of claim 9, wherein the arrangement of the plurality of electrodes facilitates controller selection of the particular electrode combination that provides for sensing of cardiac activity irrespective of changes in positional orientation of the housing within the patient.

11. The device of claim 9, wherein the arrangement of the plurality of electrodes facilitates controller selection of the particular electrode combination that provides for sensing of cardiac activity irrespective of which of the first and second faces of the housing is orientated toward the patient's skin.

12. The device of claim 9, wherein the arrangement of the plurality of electrodes facilitates controller selection of the particular electrode combination that provides for sensing of cardiac activity irrespective of both of rotation of the housing within the patient and which of the first and second faces of the housing is orientated toward the patient's skin.

13. The device of claim 9, wherein the arrangement of the plurality of electrodes facilitates controller selection of a first electrode combination that preferentially provides for sensing of cardiac activity and a second electrode combination that preferentially provides for sensing of skeletal muscle activity.

14. The device of claim 9, wherein the pulse generator is configured to deliver defibrillation or cardioversion energy.

15. The device of claim 9, wherein the controller is configured to determine cardiac rhythm states using selected electrode combinations of the plurality of electrodes.

* * * * *